United States Patent
Rabe et al.

(10) Patent No.: US 10,745,357 B2
(45) Date of Patent: Aug. 18, 2020

(54) PROCESS FOR PREPARING QUINOLIN-2-YL-PHENYLAMINE DERIVATIVES AND THEIR SALTS

(71) Applicant: RATIOPHARM GMBH, Ulm (DE)

(72) Inventors: Sebastian Rabe, Ulm (DE); Wolfgang Albrecht, Ulm (DE)

(*) Notice: Subject to any disclaimer, the term of this patent is extended or adjusted under 35 U.S.C. 154(b) by 0 days.

(21) Appl. No.: 16/671,278

(22) Filed: Nov. 1, 2019

(65) Prior Publication Data
US 2020/0062713 A1 Feb. 27, 2020

Related U.S. Application Data

(63) Continuation of application No. 16/084,891, filed as application No. PCT/EP2017/056544 on Mar. 20, 2017, now Pat. No. 10,464,903.

(30) Foreign Application Priority Data

Mar. 18, 2016 (EP) ..................... 16000661
Mar. 18, 2016 (EP) ..................... 16000662

(51) Int. Cl.
*C07D 215/38* (2006.01)
*A61P 31/18* (2006.01)

(52) U.S. Cl.
CPC ............ *C07D 215/38* (2013.01); *A61P 31/18* (2018.01)

(58) Field of Classification Search
CPC .............................. C07D 215/38; A61P 31/18
See application file for complete search history.

(56) References Cited

U.S. PATENT DOCUMENTS 10,464,903 B2 11/2019 Rabe et al.
2012/0277230 A1* 11/2012 Roux .................. C07D 215/46
514/235.2

FOREIGN PATENT DOCUMENTS

EP 2465502 A1 6/2012
WO 2010143169 A2 12/2010

OTHER PUBLICATIONS

Elder et al., The Utility of Sulfonate Salts in Drug Development, 99(7) 2948-2961 (Jul. 2010) (Year: 2010).*
Richard J. Bastin, et al., "Salt Selection and Optimisation Procedures for Pharmaceutical New Chemical Entities", Organic Process Research & Development, vol. 4, No. 5, pp. 427-435 (2000).
International Search Report issued in corresponding International Appl. No. PCT/EP2017/056544 dated May 4, 2017 (6 pages).
Written Opinion of the International Searching Authority issued in corresponding International Appl. No. PCT/EP2017/056544 dated Sep. 18, 2018 (9 pages).
A.I. Mikhalev, et al. "Synthesis and Antinflammatory and Agalgesic Activity of Isopropylamides of 2-Substituted Cinchoninic Acids", Pharmaceutical Chemistry Journal, vol. 32, No. 2, pp. 74-75 (1998).
Mino R. Caira, "Crystalline Polymorphism of Organic Compounds", Topics in Current Chemistry, vol. 198, pp. 163-208 (1998).
Hilfiker, R. et al., "Relevant of Solid-state properties for pharmaceutical products", Polymorphism in the Pharmaceutical Industry, pp. 1-19 (2006).

* cited by examiner

*Primary Examiner* — Timothy R Rozof
(74) *Attorney, Agent, or Firm* — Carter, DeLuca & Farrell LLP

(57) ABSTRACT

The present invention relates (i) to a process for the preparation of quinolin-2-yl-phenylamine derivatives of formula (I)

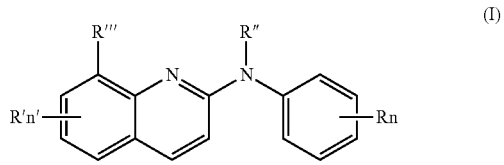

without a metal catalyst, and (ii) to soluble mineral acid or sulfonic acid salts of (8-chloro-quinolin-2-yl)-(4-trifluoromethoxyphenyl)-amine.

10 Claims, 31 Drawing Sheets

PROCESS FOR PREPARING QUINOLIN-2-YL-PHENYLAMINE DERIVATIVES AND THEIR SALTS

CROSS-REFERENCE TO RELATED APPLICATIONS

This application is a continuation of U.S. application Ser. No. 16/084,891, filed Sep. 13, 2018, which is a national stage of International Application No. PCT/EP2017/056544 filed Mar. 20, 2017, which claims priority to and the benefit of EP Application No. 16000661.5 filed on Mar. 18, 2016 and EP Application No. 16000662.3 filed on Mar. 18, 2016, the entire disclosures of each of which are incorporated herein by reference.

TECHNICAL FIELD

The present invention relates (i) to a process for the preparation of quinolin-2-yl-phenylamine derivatives of formula (I)

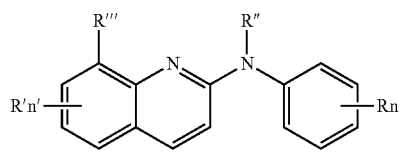

without a metal catalyst, and (ii) to soluble mineral acid or sulfonic acid salts of (8-chloro-quinolin-2-yl)-(4-trifluoromethoxyphenyl)-amine.

BACKGROUND

The international patent application WO 2010/143169 describes quinolin-2-yl-phenylamine derivatives which show inhibition of the production of the HIV core antigen p24 in HIV infected PBMCs (peripheral blood mononuclear cells). A once-day orally available first-in-class quinolin-2-yl-phenylamine derivative that inhibits HIV replication through this entirely new mechanism is (8-chloro-quinolin-2-yl)-(4-trifluoromethoxy-phenyl)-amine, also known as ABX-464. In contrast to the numerous antiviral drugs that are currently available for HIV treatment, this quinolin-2-yl-phenylamine derivative is the first agent that affects the production stage of HIV-1 replication by preventing the export of viral RNA from the nucleus to the cytoplasm in infected cells. Moreover, this drug candidate is highly selective and doesn't affect normal cellular splicing. Preclinical data indicated sustained reduction of viral load which lasted for several weeks after cessation of treatment. In phase I trials, it was well tolerated at dose levels up to 200 mg without clinically significant abnormal results. The drug candidate is currently in phase II evaluation.

The chemical structure of the drug candidate (8-chloro-quinolin-2-yl)-(4-trifluoromethoxy-phenyl)-amine, the molecular weight and formula are as follows:

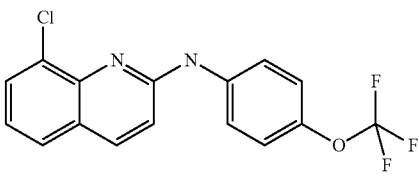

338.719
338.043
C16H10ClF3N2O

WO 2010/143169 further discloses the preparation of quinolin-2-yl-phenylamine derivatives through two routes in the presence of a metal catalyst, such as $Pd(OAc)_2$ or $Pd_2dba_3$. Example 5 describes the preparation of (8-chloro-quinolin-2-yl)-(4-trifluoromethoxy-phenyl)-amine (compound 90) according to route (A) and includes a final purification step by column chromatography to yield the pure compound.

The comparative example based on WO 2010/143169 shows that, although 2,8-dichloroquinoline was completely converted, the yield was limited to a maximum of 65%. It was further found by the inventors that simultaneous side reactions account for the relative low yield as they lead to undesired by-products. Moreover, the existence of these by-products makes pre-purification by flash chromatography inevitable. The results of the palladium mediated coupling according to Example 5 of WO 2010/143169 can be summarized as follows:

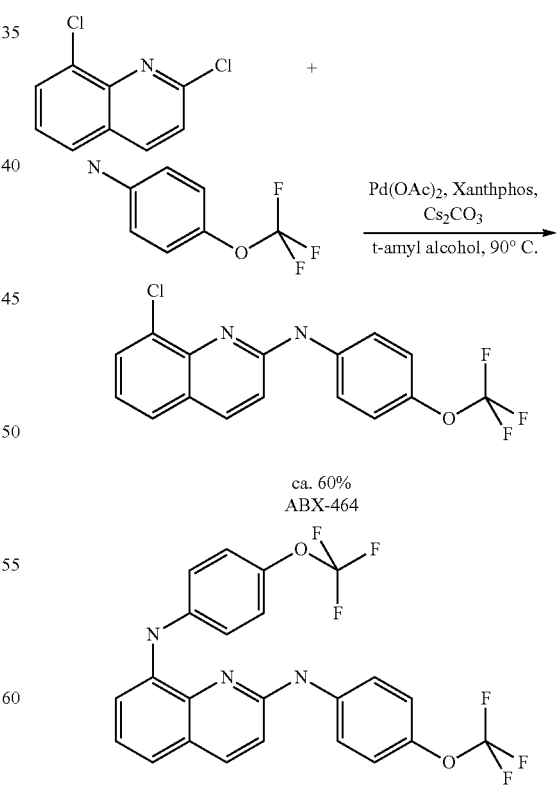

-continued

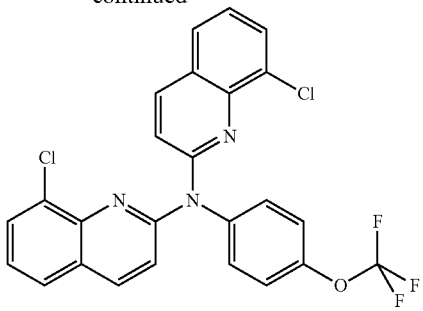

ca. 27%
Impurity 2

The rework of this procedure by the present inventors confirmed the compound, but since purification by column chromatography furnished the respective compound only in 95% purity due to undesired by-products, a recrystallization was further applied. Hereby the compound was obtained in a chemically pure crystalline form. Thereafter, the solubility of the compound was analyzed by the inventors in aqueous solutions with different pH-values simulating distinct physiological conditions. The outcome reveals a virtual insolubility of the compound in aqueous solution, independent of its pH value.

In view of the above and considering that reactions utilizing palladium as metal catalyst in the last stage are disfavored according ICH guidelines, an improved process for the preparation of quinolin-2-yl-phenylamine derivatives, and soluble forms or formulations of (8-chloro-quinolin-2-yl)-(4-trifluoromethoxy-phenyl)-amine are desired.

Therefore, the present invention concerns a process for preparing quinolin-2-yl-phenylamine derivatives, and soluble salts of (8-chloro-quinolin-2-yl)-(4-trifluoromethoxy-phenyl)-amine.

SUMMARY

According to a first embodiment, a subject-matter of the present invention relates to a process for preparing a compound of formula (I)

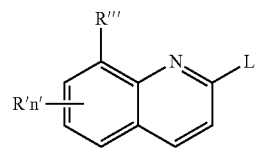

(I)

wherein:
R independently means a hydrogen atom, a halogen atom or a group selected from a $(C_1-C_3)$alkyl group, a —$NR_1R_2$ group, a $(C_1-C_3)$fluoroalkoxy group, a phenoxy group or a $(C_1-C_4)$alkoxy group, with $R_1$ and $R_2$ are independently a $(C_1-C_3)$alkyl group;
R' is a hydrogen atom, a halogen atom except fluorine, or a group selected from a $(C_1-C_3)$alkyl group, preferably a chlorine atom or a bromine atom;
R'' is a hydrogen atom or a $(C_1-C_4)$alkyl group, preferably a hydrogen group;
R''' is a hydrogen atom, a halogen atom, or a group selected from a $(C_1-C_3)$alkyl group or a $(C_1-C_4)$alkoxy group, preferably a hydrogen atom, a chlorine atom or a bromine atom;

n is 1, 2 or 3, preferably 1 or 2; and
n' is 1 or 2, preferably 1;
which comprises the step of reacting a compound of formula (II)

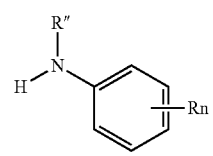

(II)

wherein:
R', R''' and n' are defined as in formula (I); and
L means a leaving group, preferably selected from a halogen atom, in particular selected from a fluorine atom, a chlorine atom or a bromine atom; preferably a fluorine atom or a chlorine atom;
with a compound of formula (III)

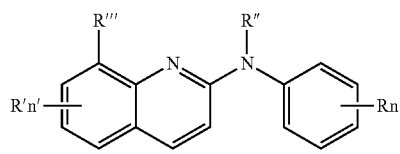

(III)

wherein R'', R, and n are defined as in formula (I); and
wherein the compound of formula (III) is present in excess and no metal catalyst is present, e.g. no palladium catalyst, such as $Pd(OAc)_2$ or $Pd_2dba_3$, as described in the prior art.

According to another aspect, the present invention relates to process for preparing a compound of formula (I) as defined above, wherein
R is a $(C_1-C_3)$fluoroalkoxy group, preferably a trifluoromethoxy group;
R' is a chlorine atom or a bromine atom;
R'' is a hydrogen atom;
R''' is a hydrogen atom, a chlorine atom or a bromine atom; and
n and n' are 1.

According to a further aspect, the present invention relates to process for preparing a compound of formula (I) as defined above, wherein
R' is a chlorine atom
R is a trifluoromethoxy group;
R'' and R''' are independently a hydrogen atom; and
n and n' are 1.

In particular, the present invention relates to a process for preparing (8-chloro-quinolin-2-yl)-(4-trifluoromethoxyphenyl)-amine and optionally its pharmaceutically acceptable salt.

The idea was to approach the desired compounds of formula (I) not by palladium mediated cross-coupling reaction but by nucleophilic aromatic substitution. This alternative reaction mechanism should avoid formation of the illustrated side products and circumvent problems with metal residues after purification. Due to the limited electron withdrawing power of the present pyridine moiety and the relative weakness of an aniline nucleophile it was surprising that the nucleophilic aromatic substitution mechanism works in the present case. However, further attempts in various solvents proceeded only with moderate conversion even at elevated temperatures.

DETAILED DESCRIPTION

According to the present invention, the ratio of solvent was reduced and the utilization of a heterogeneous inorganic base discarded. Surprisingly it was found that the basicity of the aniline derivative, in particular the 4-(trifluoromethoxy) aniline itself was sufficient, and the best result was obtained by performing the conversion in the pure aniline derivate, i.e. pure 4-(trifluoromethoxy)aniline, which proceeded very fast and clean in a spot to spot reaction. Subsequent experiments were performed with the aniline derivative and different solvents. In particular, good results were obtained with ($C_1$-$C_4$)alcohols. For example, the conversion in methanol solution proceeded very clean, but with a prolonged reaction time compared to the reaction without a solvent. With e.g. isopropanol as solvent, the reaction time was prolonged in an acceptable frame compared to the reaction without a solvent, and the conversion proceeded as clean as in the pure reactant.

Therefore, according to another aspect, the present invention relates to a process for preparing a compound of formula (I) as defined above, wherein the reaction is carried out in the presence of an ($C_1$-$C_4$)alcohol, preferably butanol or propanol, in particular t-butanol or isopropanol, more in particular isopropanol.

According to a further aspect, the present invention relates to a process for preparing a compound of formula (I) as defined above, wherein the reaction is carried out at a temperature between 25° C. and 130° C., preferably at a temperature between 80° C. and 100° C., in particular at about 90° C. According to the present invention, the term "about" means +/−5° C., i.e. from 85° C. to 95° C., preferably at 90° C.

According to a further aspect, the present invention relates to a process for preparing a compound of formula (I) as defined above, wherein the reaction is carried out for 0.5 h to 15 h, preferably for 0.5 h to 13 h, in particular for 3 h to 4 h.

According to another aspect, the present invention relates to a process for preparing a compound of formula (I) as defined above, wherein the reaction is carried out with 1 mole of compound (II) and 2-5 mole of compound (III), in particular the reaction is carried out with 1 mole of compound (II), 2-5 mole of an ($C_1$-$C_4$) alcohol, and 2-5 mole of compound (III), preferably with 1 mole of compound (II), 5 mole of an ($C_1$-$C_4$) alcohol, and 2-3 mole of compound (III).

According to a more specific aspect, the present invention relates to a process for preparing a compound of formula (I) as defined above, wherein the reaction is carried out with 1 mole of compound (II), 5 mole of an ($C_1$-$C_4$) alcohol, and 2-3 mole of compound (III) at a temperature of about 90° C., as defined above.

The isolation of the desired product can be achieved e.g. through precipitation. The reaction mixture can, therefore, be diluted with additional ($C_1$-$C_4$)alcohol, as defined above, preferably isopropanol, and after the addition of e.g. water preferably a fine and homogenous precipitate can be obtained. The collected and dried filter cake in particular yields a product in high purity (>99.0%). Preferably, before carrying out any recrystallization steps, the process according to the present invention yields a product having a purity of more than 90%, preferably more than 95%, e.g. between 95 to 99%, in particular 99%. Preferably, before carrying out any recrystallization steps, the process according to the present invention yields a product having an total impurity content of not more than 5%, preferably not more than 1%. Further purification can be obtained by recrystallization from a non-polar, aprotic solvent, e.g. cyclohexane or benzene, providing a crystalline product having a purity of ≥99.5%, preferably ≥99.9%.

Therefore, according to another aspect, the present invention relates to a process for preparing a compound of formula (I) as defined above, wherein the process further comprises the step of precipitating the compound of formula (I), preferably by adding water.

According to still another aspect, the present invention relates to a process for preparing a compound of formula (I) as defined above, wherein the process further comprises the step of recrystallizing, and optionally drying, the precipitated compound of formula (I). The recrystallization of the compound can e.g. be carried out in a non-polar, aprotic solvent, e.g. cyclohexane or benzene, preferably cyclohexane.

Generally, the herein described inventive process shows surprisingly high product selectivity, the avoidance of metal catalysts, a simple workup and a high purity grade of the isolated product. It is easily applicable for each scale (gram to multi kilogram) and shows very good reproducibility. In addition, the recrystallization of the product obtained by the inventive process provides the product in very good crystallinity.

According to another aspect, the present invention relates to a process for preparing a compound of formula (I) as defined above, wherein the process further comprises the step of preparing a pharmaceutically acceptable salt of the compound of formula (I). Suitable pharmaceutically acceptable salts are e.g. hydrobromide, trifluoroacetate, ascorbate, hydrochloride, triflate or mesylate.

According to another aspect, the present invention relates to a process for preparing a compound of formula (I) as defined above, wherein the process further comprises the step of formulating the compound of formula (I), and optionally its pharmaceutically acceptable salt, with a generally known pharmaceutically acceptable carrier, e.g. for the preparation of tablets, solutions, emulsions, microemulsions or oil-in-water emulsions, e.g. for enteral or parenteral administration, in particular for oral administration. A preferred formulation is a tablet for oral administration.

According to a second embodiment, a subject-matter of the present invention relates to a specific polymorphic form of the free base of (8-chloro-quinolin-2-yl)-(4-trifluoromethoxyphenyl)-amine, which is obtainable by a process of the present invention. The specific polymorphic form of the free base of (8-chloro-quinolin-2-yl)-(4-trifluoromethoxyphenyl)-amine is named "Form I" according to the present invention.

Form I is characterized by a single endotherm with an onset temperature of 120° C. (±2° C.) and a peak temperature of 121° (±2° C.) in the DSC thermogram (FIG. 4). In particular, Form I is alternatively or additionally characterized by characteristic signals in the x-ray powder diffractogram (FIG. 5) at angles 7.3, 14.6 and 24.8. Further characteristic signals are preferably at angles 18.3 and 23.0. Additional characteristic signals are preferably at angles 28.3 and 29.5. In another aspect, Form I is characterized by the x-ray powder diffractogram as depicted in FIG. 5.

Therefore, according to another aspect, the present invention relates to a polymorphic form of the free base of (8-chloro-quinolin-2-yl)-(4-trifluoromethoxyphenyl)-amine, characterized by a single endotherm with an onset temperature of 120° C. (±2° C.) and a peak temperature of 121° (±2° C.) in the DSC thermogram and/or characterized by characteristic signals in the x-ray powder diffractogram at angles 7.3, 14.6 and 24.8. Preferably, the polymorphic form is characterized by characteristic signals in the x-ray powder diffractogram at angles 7.3, 14.6, 18.3, 23.0 and 24.8, and in particular at angles 7.3, 14.6, 18.3, 23.0, 24.8, 28.3 and 29.5. Remarkable peaks can also be seen at angles 18.6, 22.3, 24.1, 29.0 and 42.6. In another aspect Form I is characterized by the x-ray powder diffractogram as depicted in FIG. 5.

In another aspect the present invention relates to a pharmaceutical composition comprising Form I of (8-Chloro-quinolin-2-yl)-(4-trifluoromethoxyphenyl)-amine. Preferably the pharmaceutical composition is a composition for oral administration such as a tablet.

(8-Chloro-quinolin-2-yl)-(4-trifluoromethoxyphenyl)-amine, in particular the above-described Form I, can preferably be obtained by the following process steps:
(a) preparing a mixture of 2.5 equivalents 4-(trifluoromethoxy)-aniline and 1 equivalent 2,6-dichloro-quinoline in 5 equivalents isopropanol;
(b) heating the mixture of step (a) to 90° C. for 3-4 hours;
(c) precipitating the reaction product of step (b) by the addition of isopropanol followed by the addition of water;
(d) drying the precipitated reaction product of step (c); and
(e) recrystallizing the dried reaction product of step (d) in cyclohexane.

Preferably, before carrying out any recrystallization steps, the process according to the present invention yields Form I of (8-Chloro-quinolin-2-yl)-(4-trifluoromethoxyphenyl)-amine having a purity of more than 90%, preferably more than 95%, e.g. between 95 to 99%, in particular 99%. Preferably, before carrying out any recrystallization steps, the process according to the present invention yields Form I of (8-Chloro-quinolin-2-yl)-(4-trifluoromethoxyphenyl)-amine having an total impurity content of not more than 5%, preferably not more than 1%. Further purification can be obtained by recrystallization from a non-polar, aprotic solvent, e.g. cyclohexane or benzene, providing a crystalline product having a purity of ≥99.5%, preferably ≥99.9%.

According to a third embodiment, a subject-matter of the present invention relates to a mineral acid or sulfonic acid salt of (8-chloro-quinolin-2-yl)-(4-trifluoromethoxyphenyl)-amine. The free base of the compound can e.g. be obtained according to the method disclosed in Example 5 of WO 2010/143169 or as described in the present specification.

According to another aspect, the present invention relates to mineral acid of (8-chloro-quinolin-2-yl)-(4-trifluoromethoxyphenyl)-amine, wherein the mineral acid is selected from hydrochloric acid or sulfuric acid. In a particular embodiment of the present invention the mineral acid is sulfuric acid.

According to another aspect, the present invention relates to a sulfonic acid of (8-chloro-quinolin-2-yl)-(4-trifluoromethoxyphenyl)-amine, wherein the sulfonic acid is selected from an alkylsulfonic acid or arylsulfonic acid, in particular wherein the alkylsulfonic acid is selected from mesylate, triflate or edisylate, more in particular edisylate, or wherein the arylsulfonic acid is selected from besylate or tosylate.

According to a forth embodiment, a subject-matter of the present invention relates to a pharmaceutical composition containing a mineral acid or sulfonic acid salt of (8-chloro-quinolin-2-yl)-(4-trifluoromethoxyphenyl)-amine, as defined above, and a generally known pharmaceutically acceptable carrier, e.g. for the preparation of tablets, solutions, emulsions, microemulsions or oil-in-water emulsions, e.g. for enteral or parenteral administration, in particular for oral administration. A preferred formulation is a tablet for oral administration.

According to another aspect, the present invention relates to said pharmaceutical composition for use in a method for treating an HIV infection.

In a preferred embodiment of the present invention said pharmaceutical composition is in the form of an orally administrable pharmaceutical composition, in particular for treating an HIV infection.

BRIEF DESCRIPTION OF THE DRAWINGS

The following figures and examples shall illustrate the present invention without limiting its scope.

Figures

EXAMPLES

1. Analytical Methods 1.1 HPLC/UV Chromatography
Instrument: Agilent 1200
Injection volume: 3 µl
Solvent A: acetonitrile
Solvent B: KH₂PO₄ (10 mM) pH2.3
Flow: 1.5 ml/min
Temperature: 25° C.
Column: Supelco Discovery C18, 150*4.6 mm, 5 µm

| time [min] | solvent B [%] |
|---|---|
| 0.00 | 75 |
| 4.00 | 20 |
| 15.00 | 20 |
| 15.50 | 75 |
| 17.00 | 75 |

Figure 1:
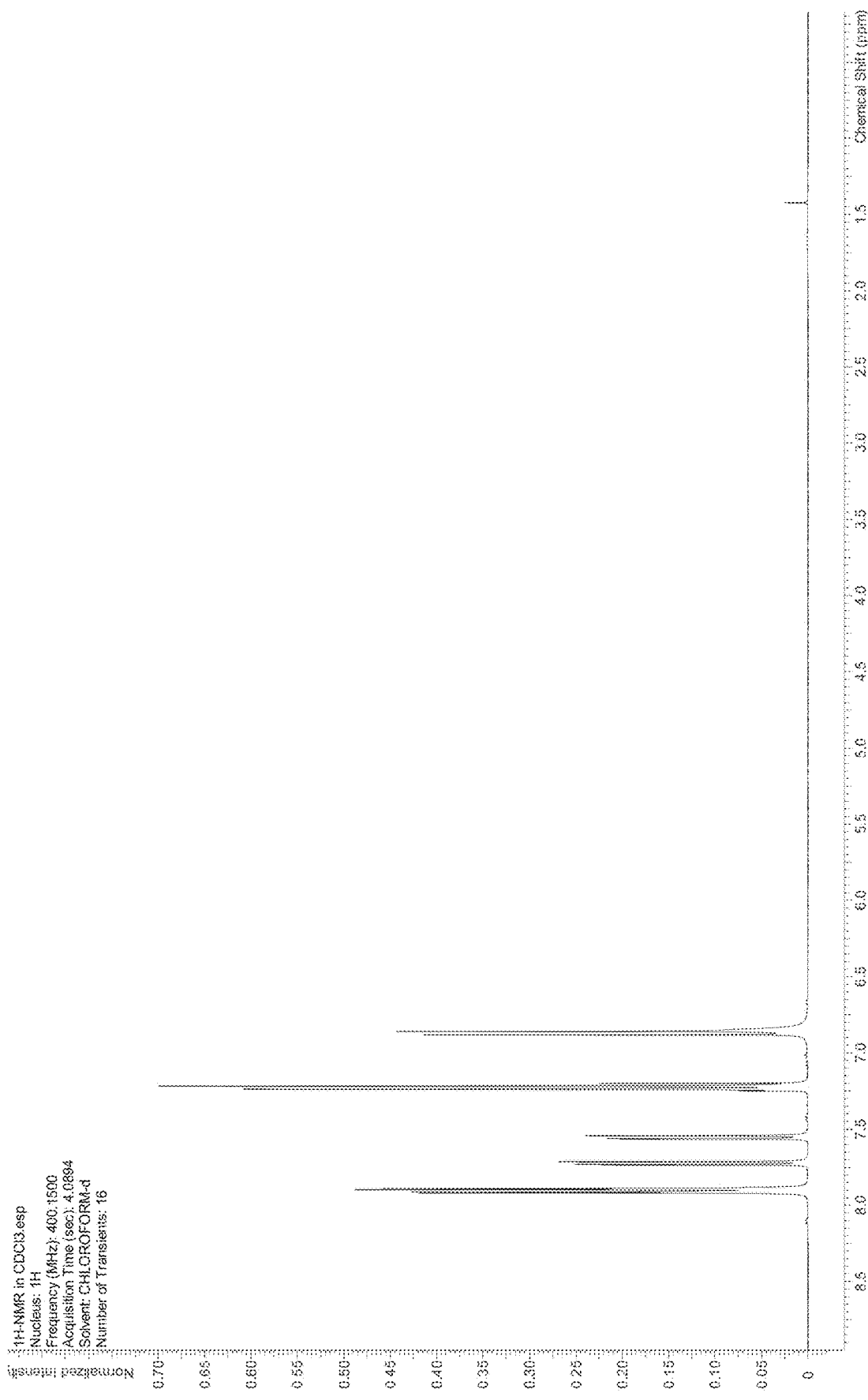
FIG. 1 shows a 1H-NMR spectrum of the free base of (8-chloro-quinolin-2-yl)-(4-trifluoromethoxyphenyl)-amine.

1.2 GC-MS
Instrument: HP6890 coupled with MS detector HP5973
Injection volume: 2 µl
Column: Agilent 19091S-431 HP-5MS UI
Injector temp: 250° C.
Injection: 2 µl
Mode: split (1/30)
Temperature program: 50-280° C., 17° C./min; runtime 15.53 min 1.3 Nuclear Magnetic Resonance (NMR) Spectroscopy
NMR-measurements were performed with Varian Mercury 400 Plus NMR
Spectrometer, Oxford AS, 400 MHz. The result is shown in FIG. 1. The NMR spectrum was characterized by the following signals:

1H NMR (400 MHz, CDCl₃) δ ppm 6.87 (m, 2H); 7.23 (m, 3H); 7.55 (dd, J=8.01, 1.28 Hz, 1H); 7.72 (dd, J=7.52, 1.28 Hz, 1H); 7.90 (m, 3H).

Figure 2:
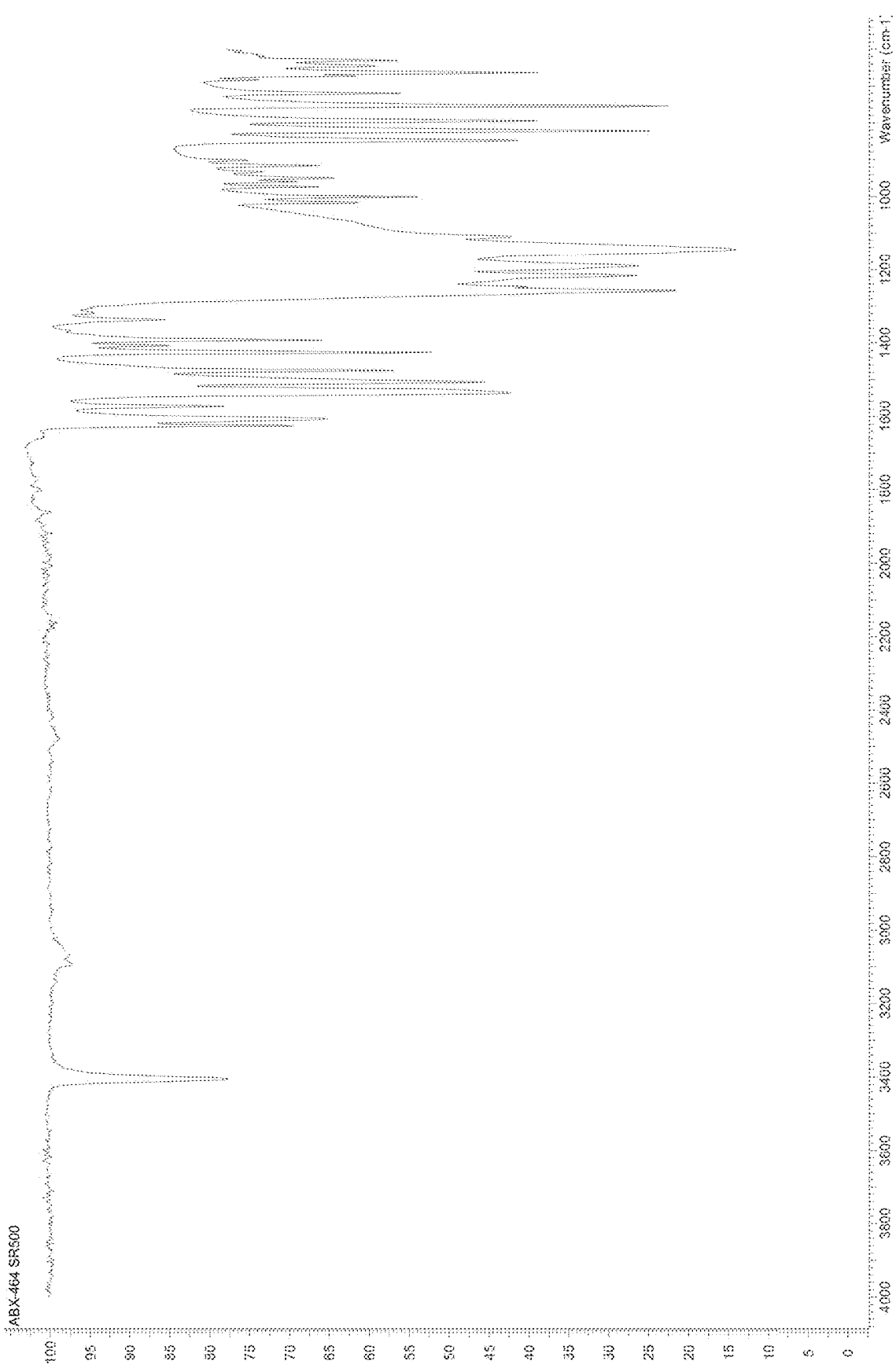
FIG. 2 shows a FT-IR spectrum of the free base of (8-chloro-quinolin-2-yl)-(4-trifluoromethoxyphenyl)-amine.

1.4 Infrared (FT-IR) Spectroscopy
IR-measurements were performed with Thermo Nicolet, Avatar 330 FT-IR. The result is shown in FIG. 2. The IR-spectrum was characterized by the following signals:

3406; 1626; 1606; 1535; 1506; 1475; 1425; 1392; 1257; 1217; 1146; 1001; 849; 822; 795; 754; 719; 673; 663; 631 cm⁻¹.

1.5 Differential Scanning Calorimetry (DSC)
Instrument: Mettler Toledo DSC 822E coupled with a Mettler Toledo Gas-Flow-Controller TS0800GC1 (Mettler-Toledo GmbH, Gießen, Germany)
Aluminium crucible: 40 µL
Lid: Perforated
Temperature range: 30° C. to 350° C.
Heating rate: 10° C./min
Nitrogen flush: 50 mL/min
Software: STARe Version. 8.10
Interpretation: Endothermic modus 1.6 X-Ray Powder Diffraction (XRPD)
The sample was analyzed on a D8 Advance X-ray powder diffractometer (Bruker-AXS, Karlsruhe, Germany). The sample holder was rotated in a plane parallel to its surface at 20 rpm during the measurement. Further conditions for the measurements are summarized in the table below. The raw data were analyzed with the program EVA (Bruker-AXS, Germany). The samples were layered onto a silicon specimen holder.

| | standard measurement |
|---|---|
| radiation | Cu Kα (λ = 1.5406 Å) |
| source | 38 kV/40 mA |
| detector | Vantec |
| detector slit | variable |
| divergence slit | v6 |
| antiscattering slit | v6 |
| 2θ range/° | 2 ≤ 2θ ≤ 55 |
| step size/° | 0.017 |

2. Preparation of (8-chloro-quinolin-2-yl)-(4-trifluoromethoxyphenyl)-amine (Comparative Example)

2,8-Dichloroquinoline (984 mg) is placed in 20 ml tert-butanol. 4-(trifluoromethoxy)aniline (743 µL) is then added in presence of 4.6 g Cs2CO3, in the presence of 58 mg Xantphos (4,5-Bis(diphenylphosphino)-9,9-dimethylxanthene), and in the presence of 22 mg Pd(OAc)₂. The reaction mixture is then heated at 90° C. and stirred during 20 hours under argon. The reaction mixture is concentrated under reduced pressure and the resulting residue is diluted with ethyl acetate. The organic phase is then washed twice with water, dried on magnesium sulphate, filtered and concentrated under reduced pressure.

The results can be summarized as follows:

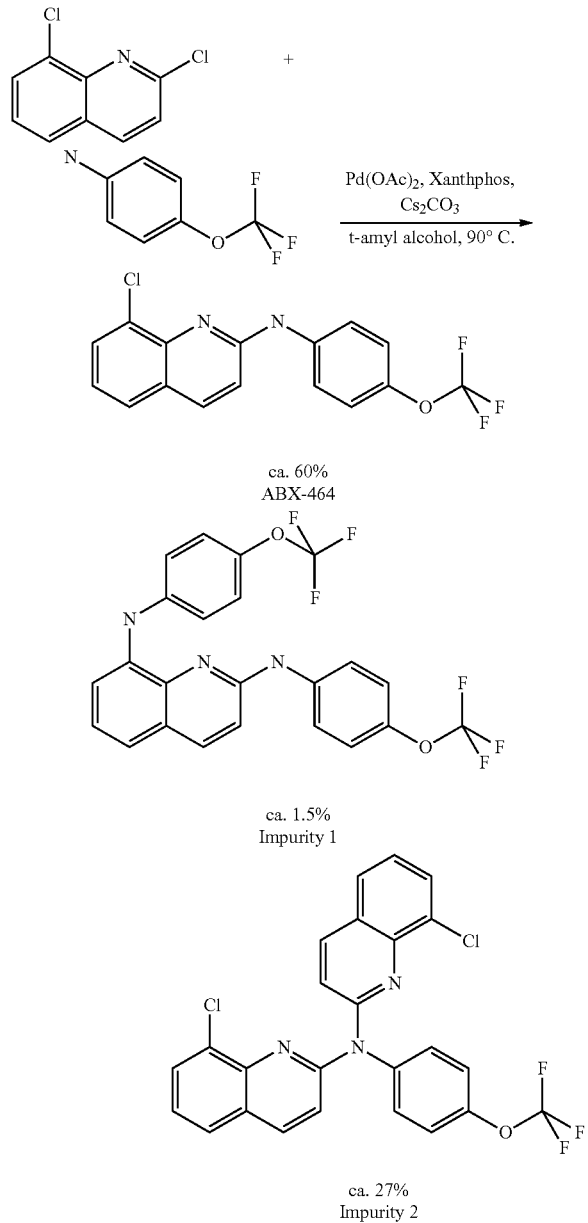

ca. 60%
ABX-464 ca. 1.5%
Impurity 1 ca. 27%
Impurity 2

3. Preparation of (8-chloro-quinolin-2-yl)-(4-trifluoromethoxyphenyl)-amine (Free Base) without a Palladium-Catalyst

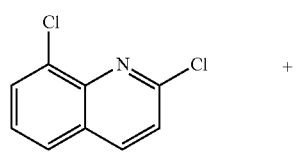

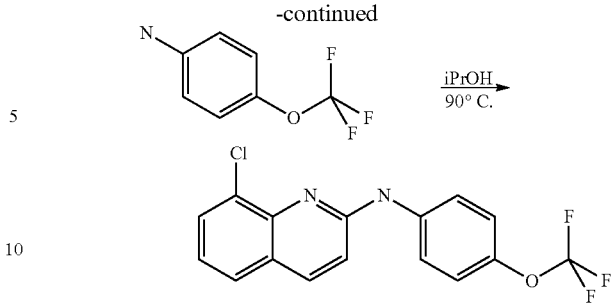

2,8-Dichloroquinoline (125 g; 0.63 mol) was slurried in 4-(trifluoromethoxy)aniline (280 g; 1.58 mol) and isopropanol (240 mL) and the mixture was heated to 90° C. The mixture was stirred for 3-4 h when HPLC indicated complete conversion of dichloroquinoline. Thereafter, additional isopropanol (730 mL) was added and the mixture cooled to approx. 40° C. Water (2.5 L) was added slowly and the resulting precipitate was collected by suction filtration. The filter cake was dried under reduced pressure and afterwards recrystallized from boiling cyclohexane (1.5 L) in order to yield pure product as an off-white solid.

Yield: 203 g (95%)

Chemical purity: 99.9% (peak area at λ=254 nm).

Figure 3:
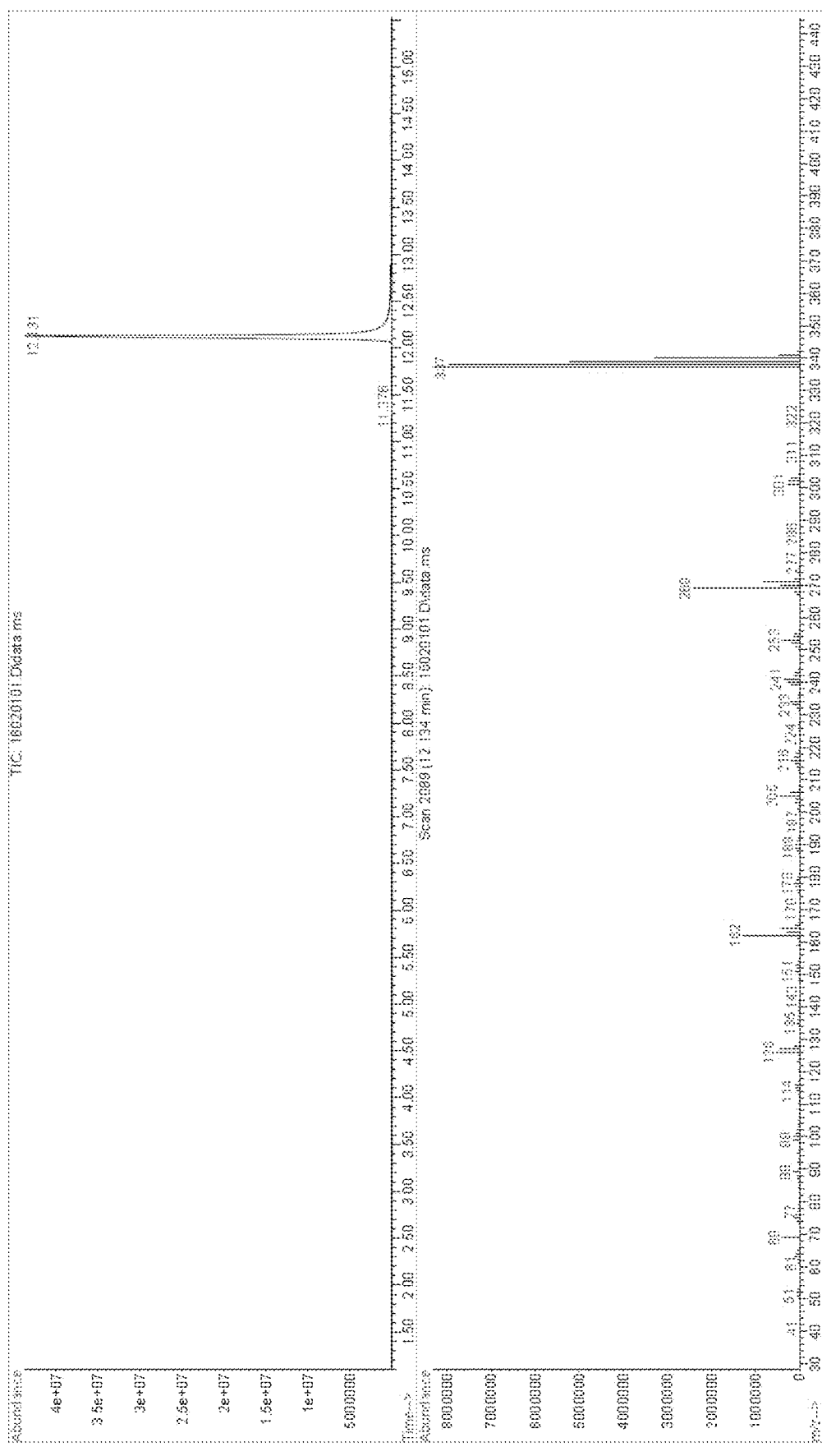
FIG. 3 shows a GC-MS spectrum of the free base of (8-chloro-quinolin-2-yl)-(4-trifluoromethoxyphenyl)-amine.

The identity of (8-chloro-quinolin-2-yl)-(4-trifluoromethoxyphenyl)-amine was verified by 1H-NMR (FIG. 1); FT-IR (FIG. 2) and GC-MS (FIG. 3).

The NMR spectrum was characterized by the following signals:

1H NMR (400 MHz, CDCl3) δ ppm 6.87 (m, 2H); 7.23 (m, 3H); 7.55 (dd, J=8.01, 1.28 Hz, 1H); 7.72 (dd, J=7.52, 1.28 Hz, 1H); 7.90 (m, 3H).

The IR-spectrum was characterized by the following signals:

3406; 1626; 1606; 1535; 1506; 1475; 1425; 1392; 1257; 1217; 1146; 1001; 849; 822; 795; 754; 719; 673; 663; 631 cm$^{-1}$.

Figure 4:
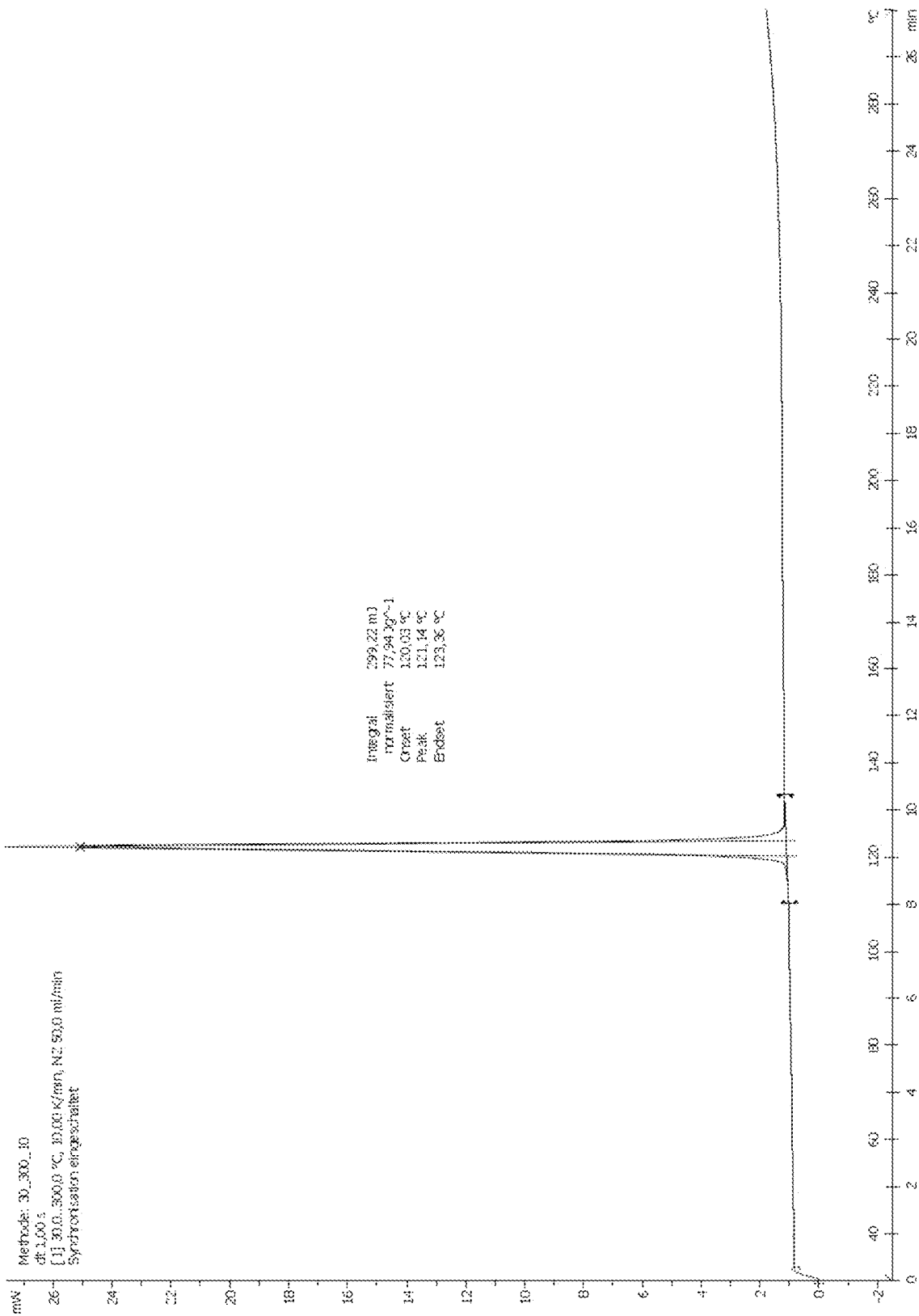
FIG. 4 shows a DSC thermogram of the free base of (8-chloro-quinolin-2-yl)-(4-trifluoromethoxyphenyl)-amine.

The solid state characteristics were investigated by means of DSC and XRPD and is as follows:

The DSC thermogram (FIG. 4) is characterized by a single endotherm with an onset temperature of 120° C. (±2° C.) and a peak temperature of 121° (±2° C.).

Figure 5:
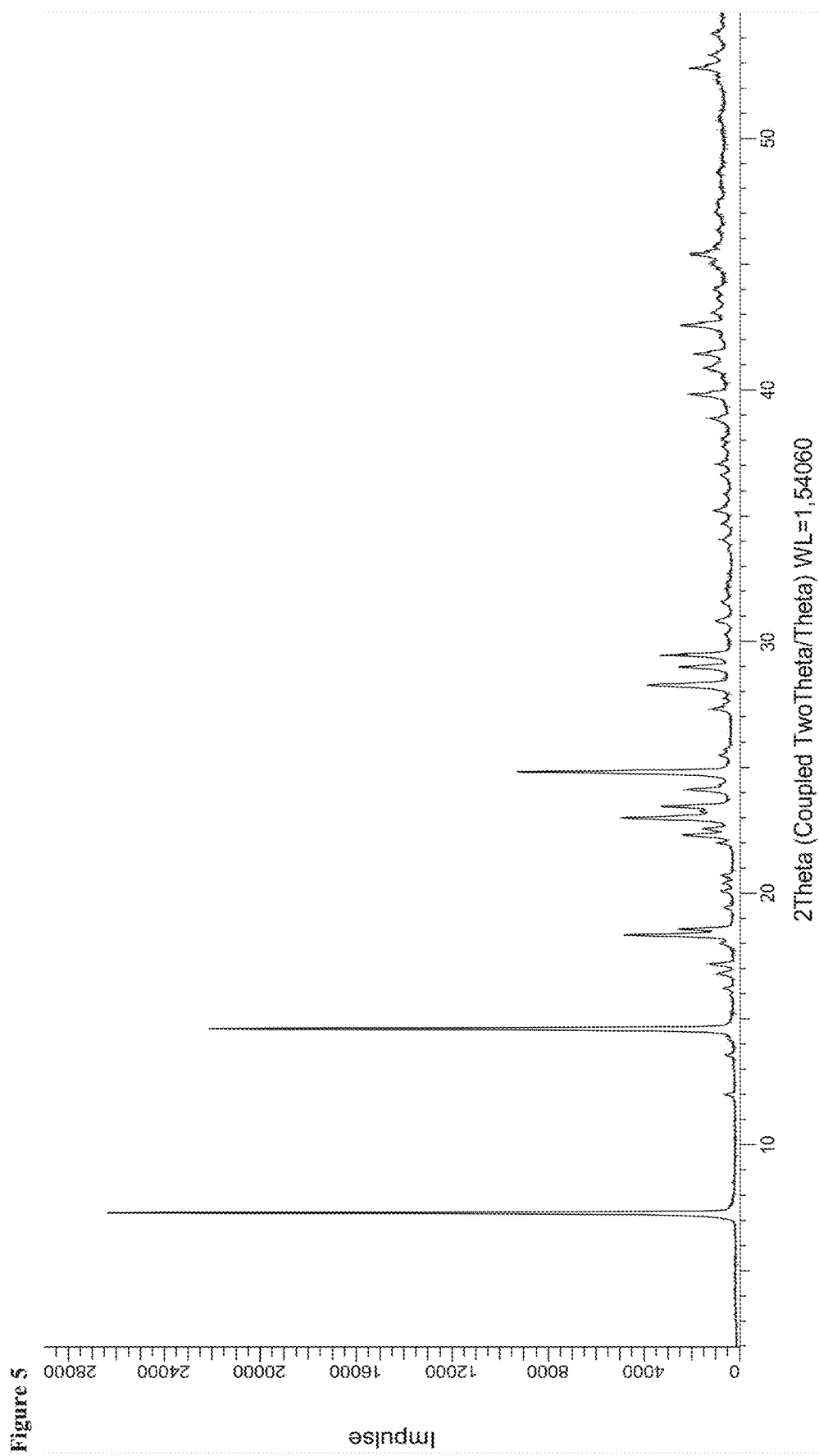
FIG. 5 shows a XRPD diffractogram of the free base of (8-chloro-quinolin-2-yl)-(4-trifluoromethoxyphenyl)-amine.

A characteristic x-ray powder diffractogram is given in FIG. 5 and its characteristic signals are summarized in the following table:

| Index | Angle | Relative Intensity |
| --- | --- | --- |
| 1 | 7.3 | 100.0% |
| 2 | 12.0 | 1.5% |
| 3 | 13.6 | 1.5% |
| 4 | 14.6 | 86.4% |
| 5 | 16.2 | 1.6% |
| 6 | 16.8 | 2.6% |
| 7 | 17.2 | 3.7% |
| 8 | 18.0 | 1.9% |
| 9 | 18.3 | 18.3% |
| 10 | 18.6 | 8.2% |
| 11 | 19.4 | 1.4% |
| 12 | 20.1 | 1.9% |
| 13 | 20.4 | 1.5% |
| 14 | 20.7 | 1.7% |
| 15 | 22.0 | 1.7% |
| 16 | 22.3 | 8.0% |
| 17 | 22.6 | 4.7% |
| 18 | 23.0 | 18.1% |
| 19 | 23.3 | 4.8% |

| Index | Angle | Relative Intensity |
|---|---|---|
| 20 | 23.5 | 11.5% |
| 21 | 24.1 | 7.1% |
| 22 | 24.8 | 35.1% |
| 23 | 25.5 | 1.9% |
| 24 | 27.3 | 3.0% |
| 25 | 27.4 | 2.3% |
| 26 | 28.3 | 13.8% |
| 27 | 29.0 | 8.6% |
| 28 | 29.5 | 11.2% |
| 29 | 30.8 | 2.5% |
| 30 | 31.6 | 1.4% |
| 31 | 34.1 | 1.8% |
| 32 | 34.7 | 1.8% |
| 33 | 35.2 | 2.6% |
| 34 | 35.9 | 0.6% |
| 35 | 36.6 | 1.5% |
| 36 | 37.1 | 2.0% |
| 37 | 38.9 | 2.8% |
| 38 | 39.8 | 5.6% |
| 39 | 40.9 | 3.5% |
| 40 | 41.5 | 5.0% |
| 41 | 42.6 | 7.4% |
| 42 | 45.4 | 5.4% |
| 43 | 52.8 | 4.9% |

Major peaks can be seen at angles 7.3, 14.6 and 18.3 with relative intensities of 100.0%, 86.4% and 18.3%, respectively. Further prominent peaks can be seen at angles 23.0 and 24.8 with relative intensities of 18.1% and 35.1%, respectively. Additional prominent peaks can be seen at angles 28.3 and 29.5 with relative intensities of 13.8% and 11.2%. Finally, remarkable peaks can be seen at angles 18.6, 22.3, 24.1, 29.0 and 42.6 with relative intensities of 8.2%, 8.0%, 7.1%, 8.6% and 7.4%, respectively.

4. Comparison of Reaction Conditions

Subsequent experiments were performed as outlined in the following table:

| eq 2,8-Dichloro-quinoline | eq 4-(Trifluoro-methoxy)-aniline | Base | Solvent | Temp [° C.] | Reaction Time [h] | Product Conversion[a] |
|---|---|---|---|---|---|---|
| 1 | 1.5 | 4 eq K$_2$CO$_3$ | 30 eq DMF | 140 | 24 | 3.5% |
| 1 | 1.5 | 4 eq K$_2$CO$_3$ | 30 eq DMSO | 140 | 24 | 3.5% |
| 1 | 1.5 | 4 eq K$_2$CO$_3$ | 30 eq NMP | 140 | 24 | 1.5% |
| 1 | 1.5 | 4 eq K$_2$CO$_3$ | 40 eq MeOH | 70 | 12 | — |
| 1 | 2 | 4 eq TEA | 30 eq THF | 70 | 15 | — |
| 1 | 2 | 4 eq TEA | 30 eq BuOH | 120 | 15 | 0.5% |
| 1 | 2.5 | — | 10 eq DMF | 140 | 3 | 67% |
| 1 | 2.5 | — | 10 eq DMSO | 140 | 3 | 79% |
| 1 | 2.5 | — | 10 eq NMP | 140 | 3 | 95% |
| 1 | 2.5 | — | 10 eq MeOH | 70 | 13 | 98.5% |
| 1 | 5 | — | — | 130 | 0.5 | 99.5% |
| 1 | 2.5 | — | 5 eq iPrOH | 90 | 4 | 99.5% |

[a]estimates by HPLC (230 nm)

DMF, DMSO and NMP solutions performed a rapid conversion of starting material into (8-chloro-quinolin-2-yl)-(4-trifluoromethoxyphenyl)-amine, but simultaneously the mixtures colored dark or intensive purpure (DMSO) evoked by formation of numerous by-products. In contrast, the conversion in MeOH solution proceeded very clean, but much more time consuming. At last the best result was obtained by performing the conversion in pure 4-(trifluoromethoxy)aniline (5 eq) which proceeded very fast and clean in a spot to spot reaction.

An even lower amount of the aniline would enable a satisfying conversion too, but 5 equivalents roughly represent the lowest volume for successful dissolution of 2,8-dichloroquinoline. Finally, 2.5 eq of 4-(trifluoromethoxy)aniline mixed with 5 eq of isopropanol (IPA) were established successfully. The reaction time was prolonged in an acceptable frame, and the conversion proceeded as clean as in the pure reactant.

5. Preparation of (8-chloro-quinolin-2-yl)-(4-trifluoromethoxyphenyl)-amine (HCl Addition Salt)

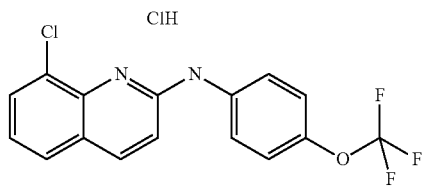 [SMILES: Cl ; FC(F)(F)Oc1ccc(Nc2ccc3cccc(Cl)c3n2)cc1]

(8-Chloro-quinolin-2-yl)-(4-trifluoromethoxyphenyl)-amine (5 g; 14.8 mmol) was dissolved in diethyl ether (200 mL) at room temperature and HCl (15 mL; 2 M in Et$_2$O) was added subsequently. The resulting slurry was stirred for 30 min before the precipitate was filtered off and dried under reduced pressure. The HCl addition salt was obtained as a pale yellow solid.

Yield: 4.3 g (78%).

Chemical purity: 99.9% (peak area at λ=254 nm).

Figure 6:
FIG. 6 shows a 1H-NMR spectrum of the HCl addition salt of (8-chloro-quinolin-2-yl)-(4-trifluoromethoxyphenyl)-amine.
Figure 7:
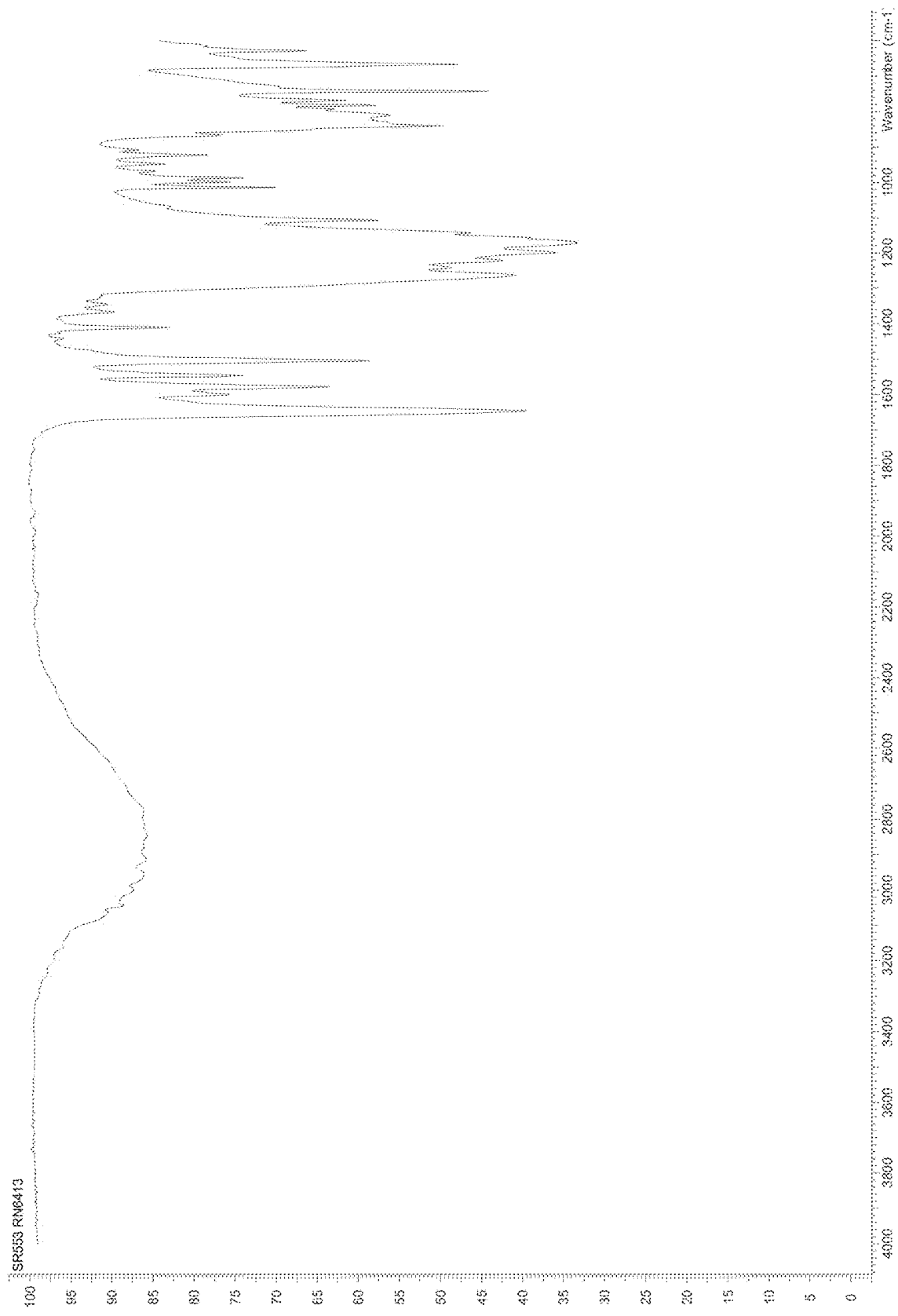
FIG. 7 shows a FT-IR spectrum of the HCl addition salt of (8-chloro-quinolin-2-yl)-(4-trifluoromethoxyphenyl)-amine.

The identity of the HCl addition salt was verified by 1H-NMR (FIG. 6) and FT-IR (FIG. 7).

The NMR spectrum was characterized by the following signals:

1H NMR (400 MHz, DMSO-d6) δ ppm 7.17 (d, J=8.60 Hz, 1H); 7.29 (t, J=7.82 Hz, 1H); 7.34 (d, J=8.60 Hz, 2H); 7.71-7.76 (m, 1H); 7.76-7.80 (m, 1H); 8.15 (d, J=8.99 Hz, 1H); 8.32 (m, 2H); 10.14 (m, 2H).

The IR-spectrum was characterized by the following signals:

1645; 1577; 1547; 1504; 1409; 1263; 1199; 1172; 1107; 1014; 999; 987; 922; 840; 783; 767; 742; 667; 628 cm$^{-1}$.

Figure 16:
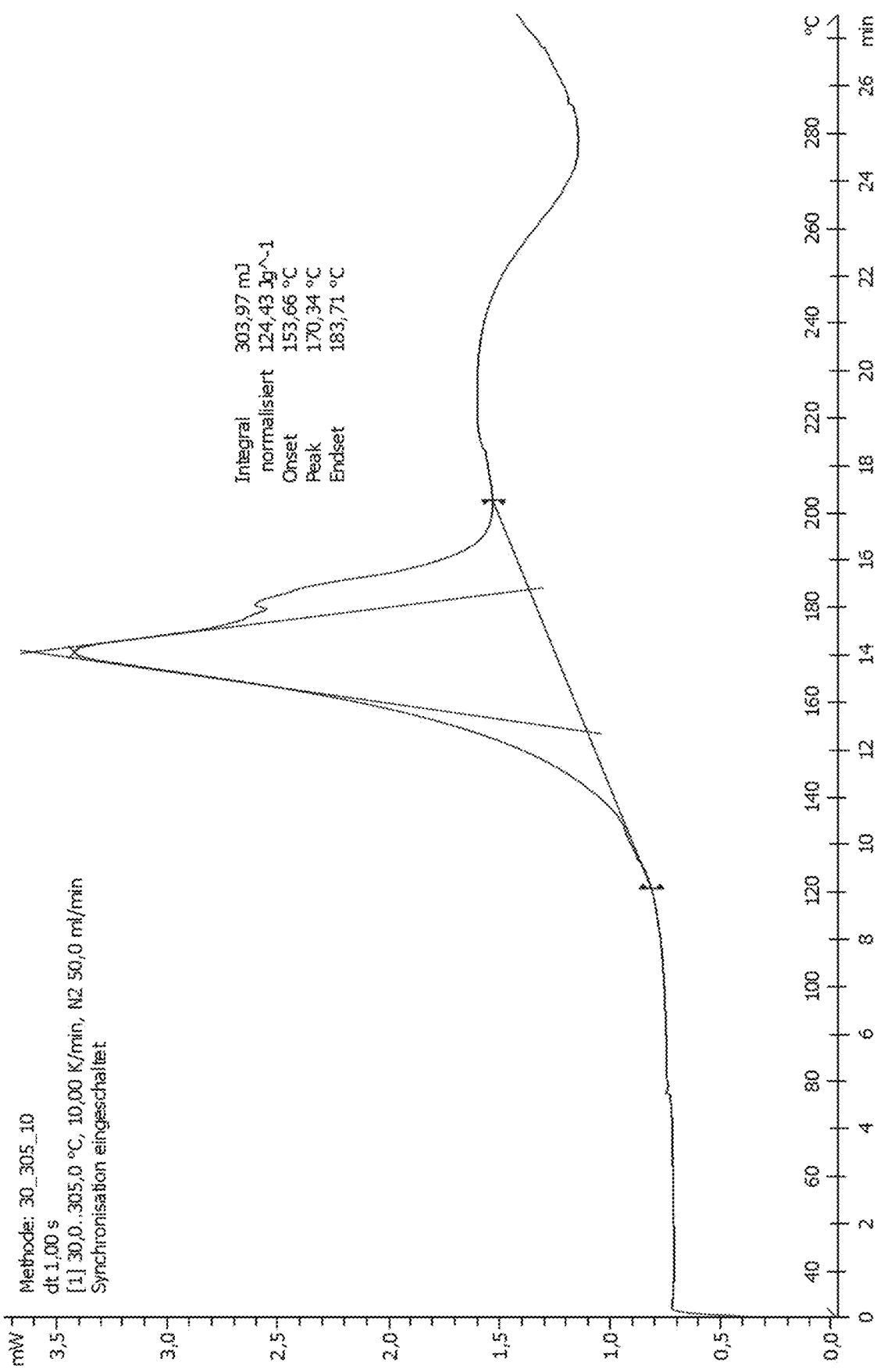
FIG. 16 shows a DSC thermogram of the HCl addition salt of (8-chloro-quinolin-2-yl)-(4-trifluoromethoxyphenyl)-amine.

The solid state characteristics were investigated by means of DSC and XRPD and is as follows:

The DSC thermogram (FIG. 16) is characterized by a single broad endotherm with an onset temperature of 154° C. (±5° C.) and a peak temperature of 170° (±5° C.).

Figure 17:
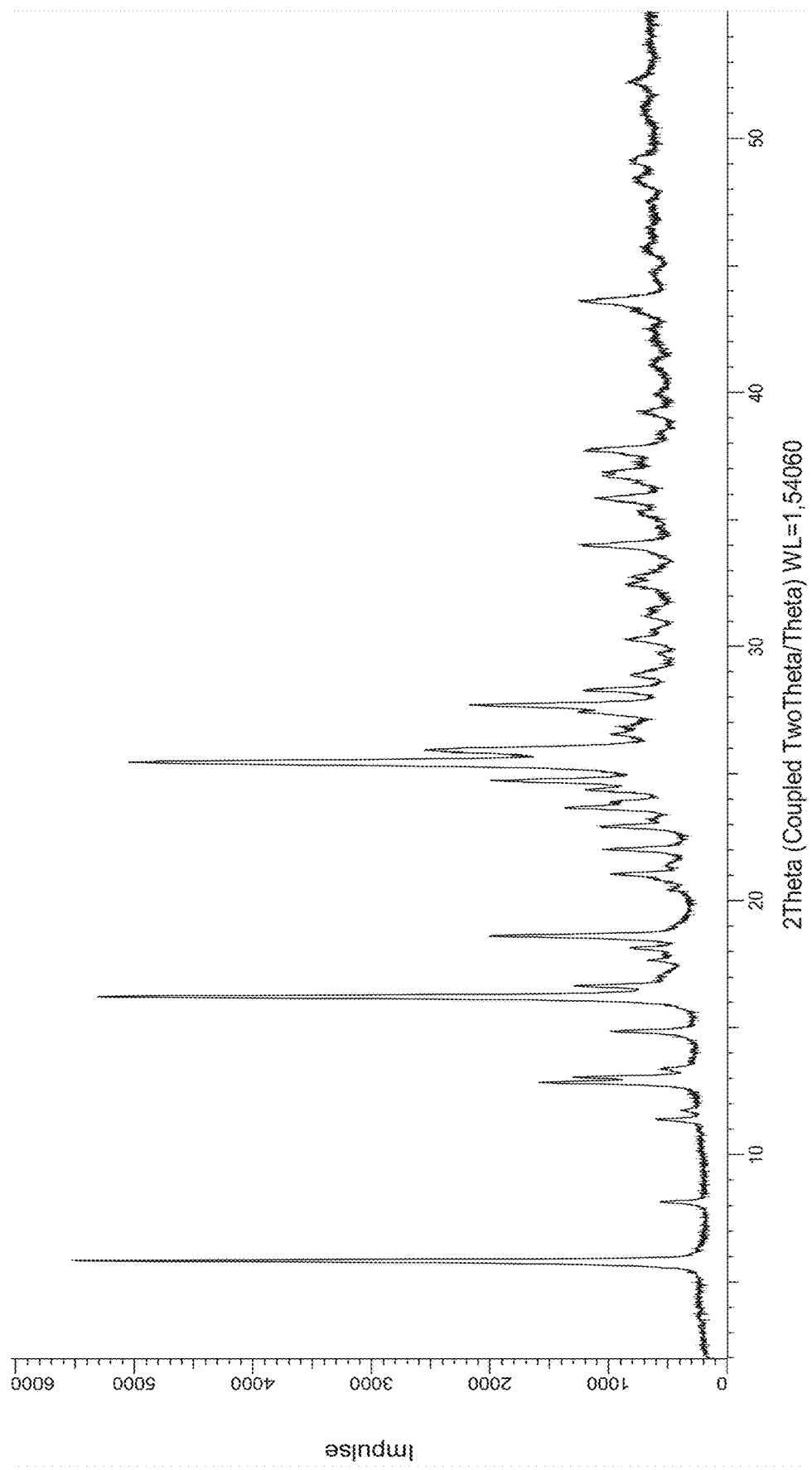
FIG. 17 shows a XRPD diffractogram of the HCl addition salt of (8-chloro-quinolin-2-yl)-(4-trifluoromethoxyphenyl)-amine.

A characteristic x-ray powder diffractogram is given in FIG. 17 and its characteristic signals are summarized in the following table:

| Index | Angle | Relative Intensity |
|---|---|---|
| 1 | 5.8 | 100.0% |
| 2 | 8.2 | 7.0% |
| 3 | 11.4 | 7.0% |
| 4 | 11.8 | 2.9% |

| Index | Angle | Relative Intensity |
|---|---|---|
| 5 | 12.9 | 26.1% |
| 6 | 13.0 | 16.7% |
| 7 | 13.4 | 5.5% |
| 8 | 14.9 | 13.5% |
| 9 | 16.2 | 98.0% |
| 10 | 16.7 | 18.2% |
| 11 | 17.7 | 6.3% |
| 12 | 18.1 | 8.7% |
| 13 | 18.6 | 31.9% |
| 14 | 21.1 | 12.3% |
| 15 | 22.0 | 13.4% |
| 16 | 22.9 | 13.2% |
| 17 | 23.7 | 18.0% |
| 18 | 24.4 | 14.0% |
| 19 | 24.7 | 28.7% |
| 20 | 25.5 | 86.2% |
| 21 | 25.9 | 39.7% |
| 22 | 27.5 | 13.4% |
| 23 | 27.7 | 30.7% |
| 24 | 28.3 | 13.9% |
| 25 | 34.0 | 13.4% |
| 26 | 35.9 | 11.5% |
| 27 | 37.7 | 13.7% |
| 28 | 43.6 | 13.3% |

| Index | Angle | Relative Intensity |
|---|---|---|
| 1 | 6.7 | 41.9% |
| 2 | 7.3 | 17.7% |
| 3 | 9.0 | 9.2% |
| 4 | 10.5 | 16.6% |
| 5 | 11.2 | 20.2% |
| 6 | 11.6 | 89.5% |
| 7 | 13.2 | 11.7% |
| 8 | 13.8 | 38.6% |
| 9 | 15.6 | 82.9% |
| 10 | 15.9 | 62.0% |
| 11 | 16.8 | 52.4% |
| 12 | 17.3 | 100.0% |
| 13 | 17.8 | 50.1% |
| 14 | 19.7 | 27.3% |
| 15 | 20.3 | 90.2% |
| 16 | 22.1 | 81.9% |
| 17 | 22.5 | 65.5% |
| 18 | 22.7 | 58.7% |
| 19 | 24.0 | 67.8% |
| 20 | 24.5 | 58.6% |
| 21 | 24.7 | 52.9% |
| 22 | 26.4 | 56.7% |
| 23 | 27.3 | 22.7% |
| 24 | 28.3 | 31.3% |

6. Preparation of (8-chloro-quinolin-2-yl)-(4-trifluoromethoxyphenyl)-amine ($H_2SO_4$ Addition Salt)

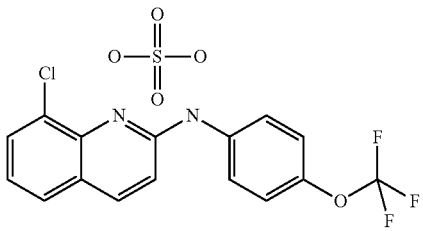

(8-Chloro-quinolin-2-yl)-(4-trifluoromethoxyphenyl)-amine (5 g; 14.8 mmol) was dissolved in diethyl ether (200 mL) at room temperature and $H_2SO_4$ (0.9 mL; 16.2 mmol) was added subsequently. The resulting slurry was stirred for 30 min before the precipitate was filtered off and dried under reduced pressure. The $H_2SO_4$ addition salt was obtained as a gray solid.

Yield: 6.4 g (99%).

Chemical purity: 99.9% (peak area at λ=254 nm).

Figure 8:
FIG. 8 shows a 1H-NMR spectrum of the $H_2SO_4$ addition salt of (8-chloro-quinolin-2-yl)-(4-trifluoromethoxyphenyl)-amine.
Figure 9:
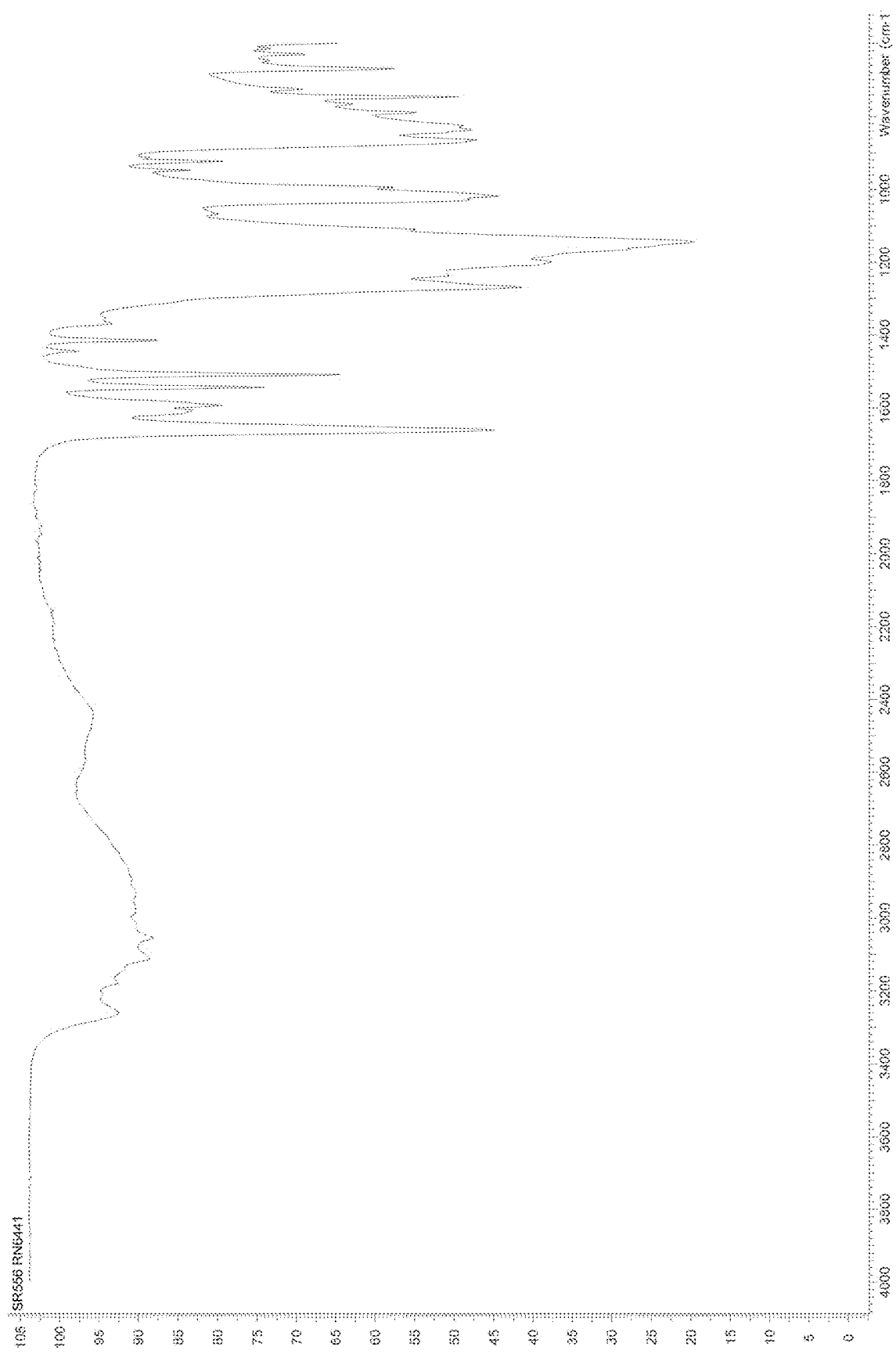
FIG. 9 shows a FT-IR spectrum of the $H_2SO_4$ addition salt of (8-chloro-quinolin-2-yl)-(4-trifluoromethoxyphenyl)-amine.

The identity of the $H_2SO_4$ addition salt was verified by $^1$H-NMR (FIG. 8) and FT-IR (FIG. 9).

The NMR spectrum was characterized by the following signals:

1H NMR (400 MHz, DMSO-d6) δ ppm 7.17 (d, J=8.93 Hz, 1H); 7.23-7.46 (m, 3H); 7.75-7.81 (m, 2H); 8.17 (d, J=8.93 Hz, 1H); 8.30 (m, 2H); 9.41 (br s, 2H); 9.94 (s, 1H)

The IR-spectrum was characterized by the following signals:

1660; 1508; 1269; 1144; 1018; 993; 864; 746; 669 cm$^{-1}$.

Figure 18:
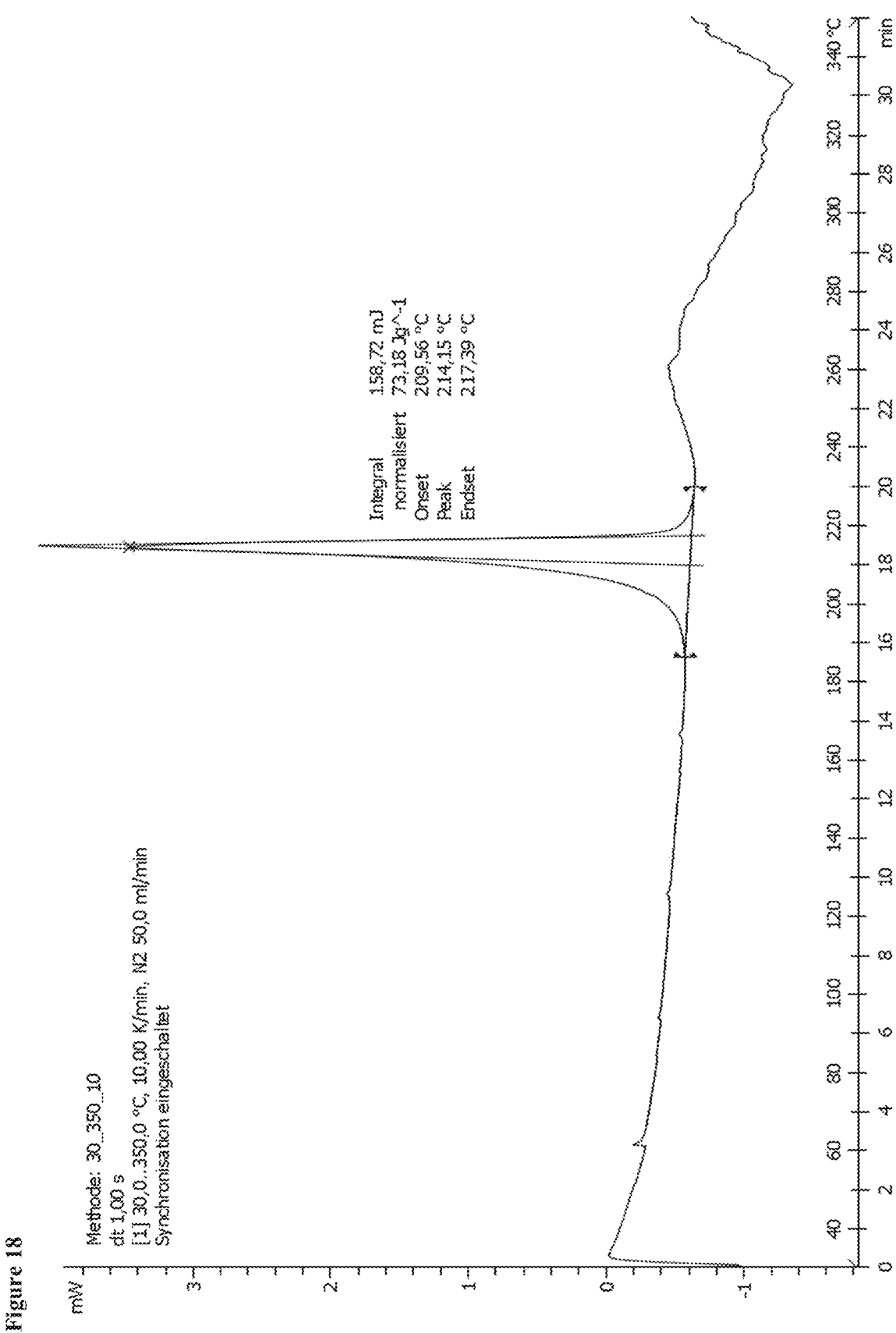
FIG. 18 shows a DSC thermogram of the H₂SO₄ addition salt of (8-chloro-quinolin-2-yl)-(4-trifluoromethoxyphenyl)-amine.

The solid state characteristics were investigated by means of DSC and XRPD and is as follows:

The DSC thermogram (FIG. 18) is characterized by a single broad endotherm with an onset temperature of 209° C. (±5° C.) and a peak temperature of 214° (±5° C.).

Figure 19:
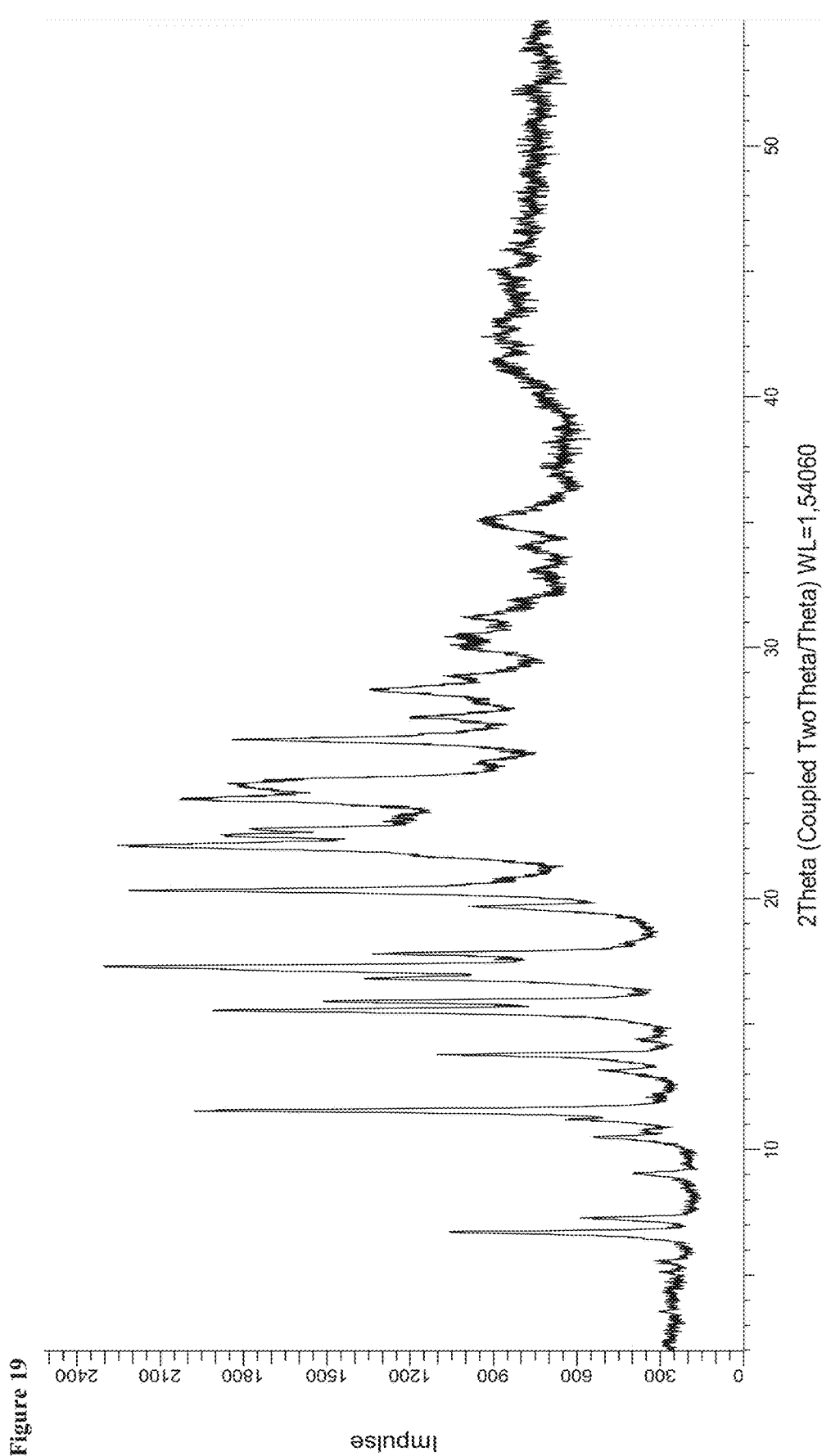
FIG. 19 shows a XRPD diffractogram of the H₂SO₄ addition salt of (8-chloro-quinolin-2-yl)-(4-trifluoromethoxyphenyl)-amine.

A characteristic x-ray powder diffractogram is given in FIG. 19 and its characteristic signals are summarized in the following table:

7. Preparation of (8-chloro-quinolin-2-yl)-(4-trifluoromethoxyphenyl)-amine (Besylate Addition Salt)

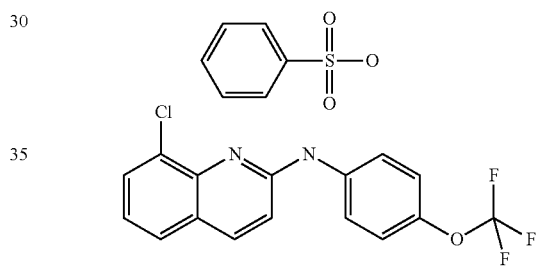

(8-Chloro-quinolin-2-yl)-(4-trifluoromethoxyphenyl)-amine (5 g; 14.8 mmol) was dissolved in diethyl ether (200 mL) at room temperature and benzenesulfonic acid (2.57 g; 16.2 mmol) dissolved in dichloromethane (10 mL) was added subsequently. The resulting slurry was stirred for 30 min before the precipitate was filtered off and dried under reduced pressure. The $PhSO_3H$ addition salt was obtained as a pale yellow solid.

Yield: 7.2 g (98.2%).

Chemical purity: 99.9% (peak area at λ=254 nm).

Figure 10:
FIG. 10 shows a 1H-NMR spectrum of the besylate addition salt of (8-chloro-quinolin-2-yl)-(4-trifluoromethoxyphenyl)-amine.
Figure 11:
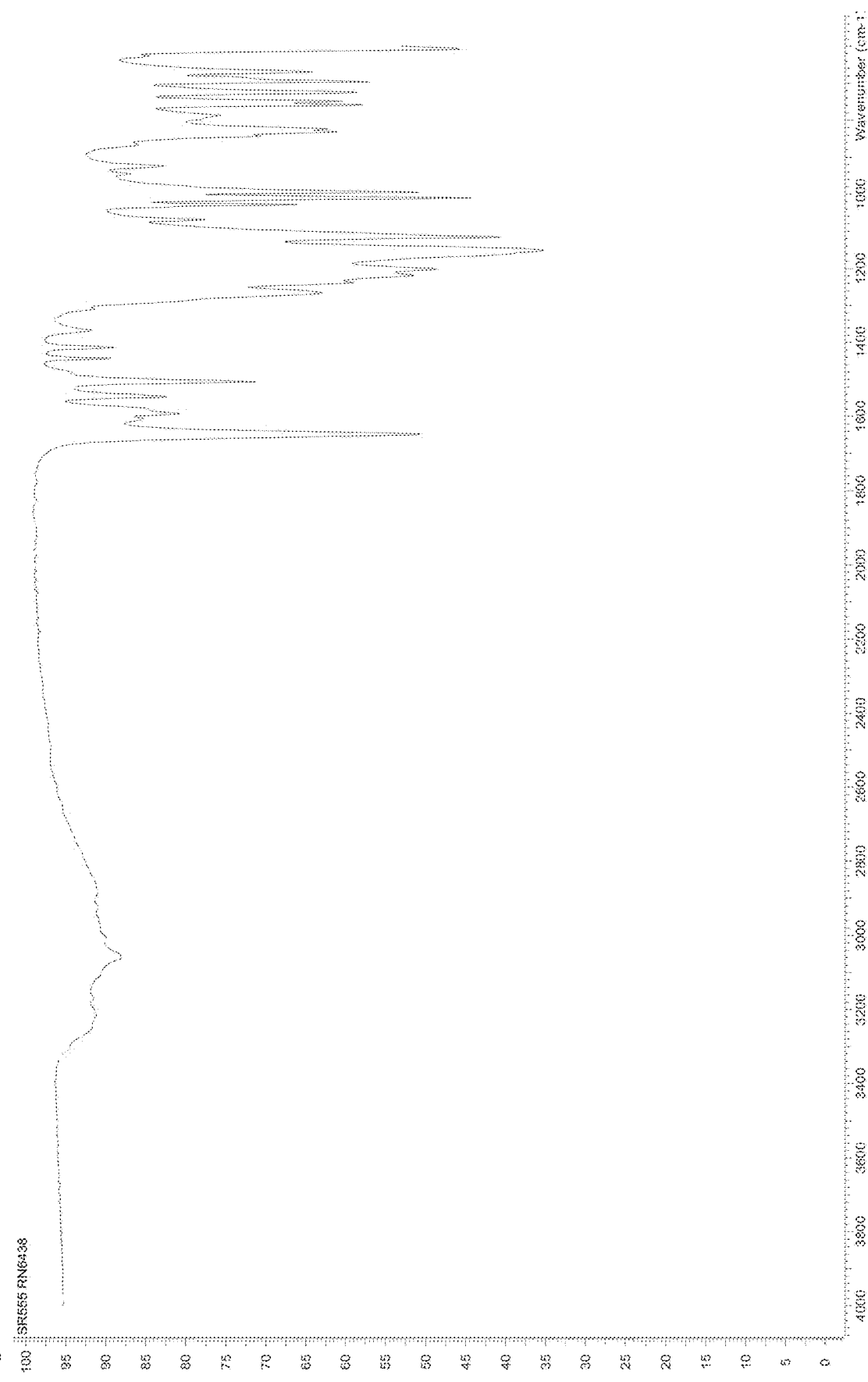
FIG. 11 shows a FT-IR spectrum of the besylate addition salt of (8-chloro-quinolin-2-yl)-(4-trifluoromethoxyphenyl)-amine.

The identity of the besylate addition salt was verified by 1H-NMR (FIG. 10) and FT-IR (FIG. 11).

The NMR spectrum was characterized by the following signals:

1H NMR (400 MHz, DMSO-d6) δ ppm 7.17 (d, J=8.93 Hz, 1H); 7.23-7.43 (m, 6H); 7.56-7.67 (m, 2H) 7.78-7.81 (m, 2H); 8.17 (d, J=9.05 Hz, 1H); 8.24-8.38 (m, 2H); 9.96 (s, 1H) 11.98 (br s, 1H).

The IR-spectrum was characterized by the following signals:

1647; 1506; 1151; 1116; 1028; 1010; 995; 923; 831; 758; 748; 725; 696; 669; 607 cm$^{-1}$.

Figure 20:
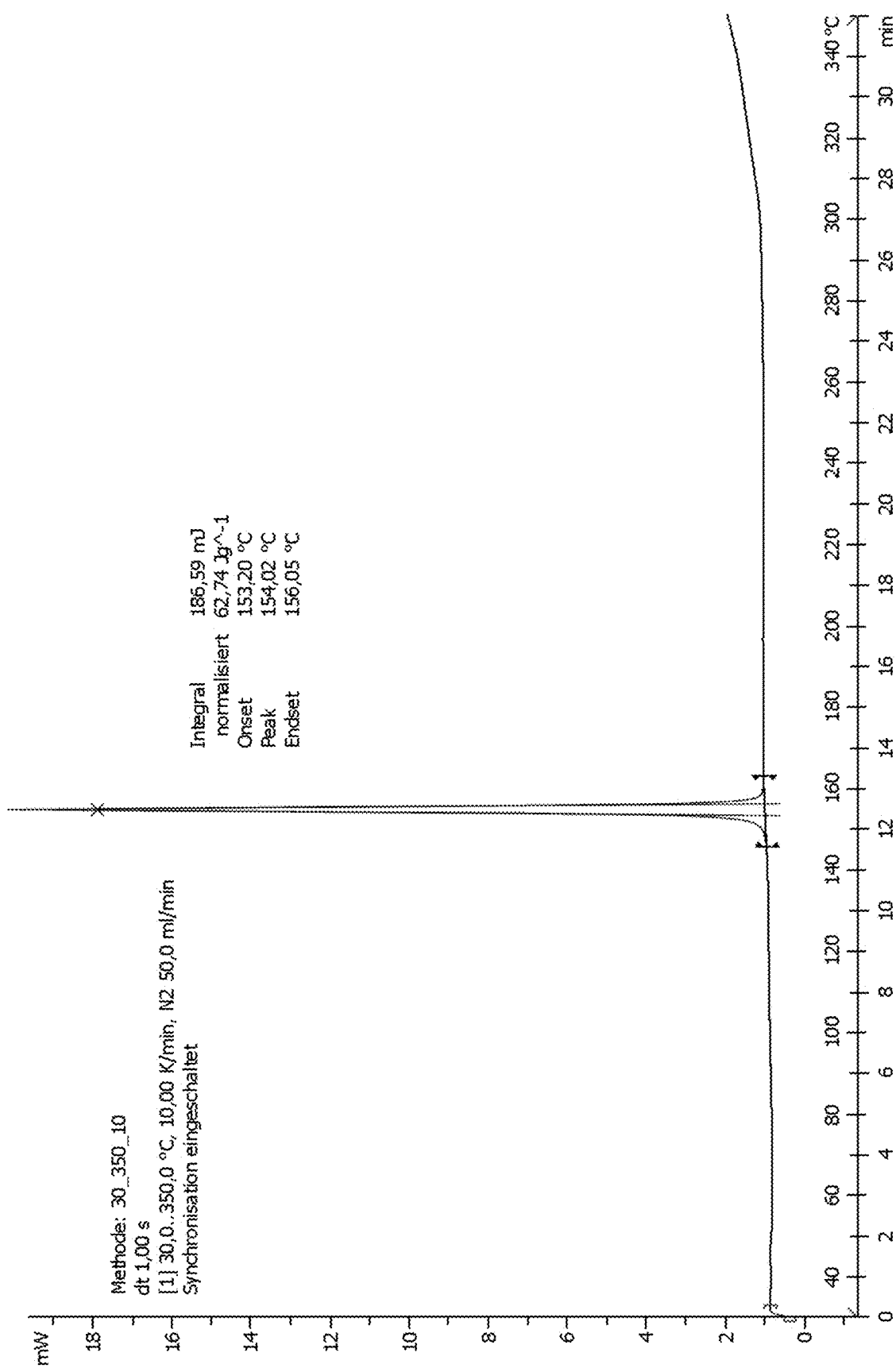
FIG. 20 shows a DSC thermogram of the besylate addition salt of (8-chloro-quinolin-2-yl)-(4-trifluoromethoxyphenyl)-amine.

The solid state characteristics were investigated by means of DSC and XRPD and is as follows:

The DSC thermogram (FIG. 20) is characterized by a single endotherm with an onset temperature of 153° C. (±5° C.) and a peak temperature of 154° (±5° C.).

Figure 21:
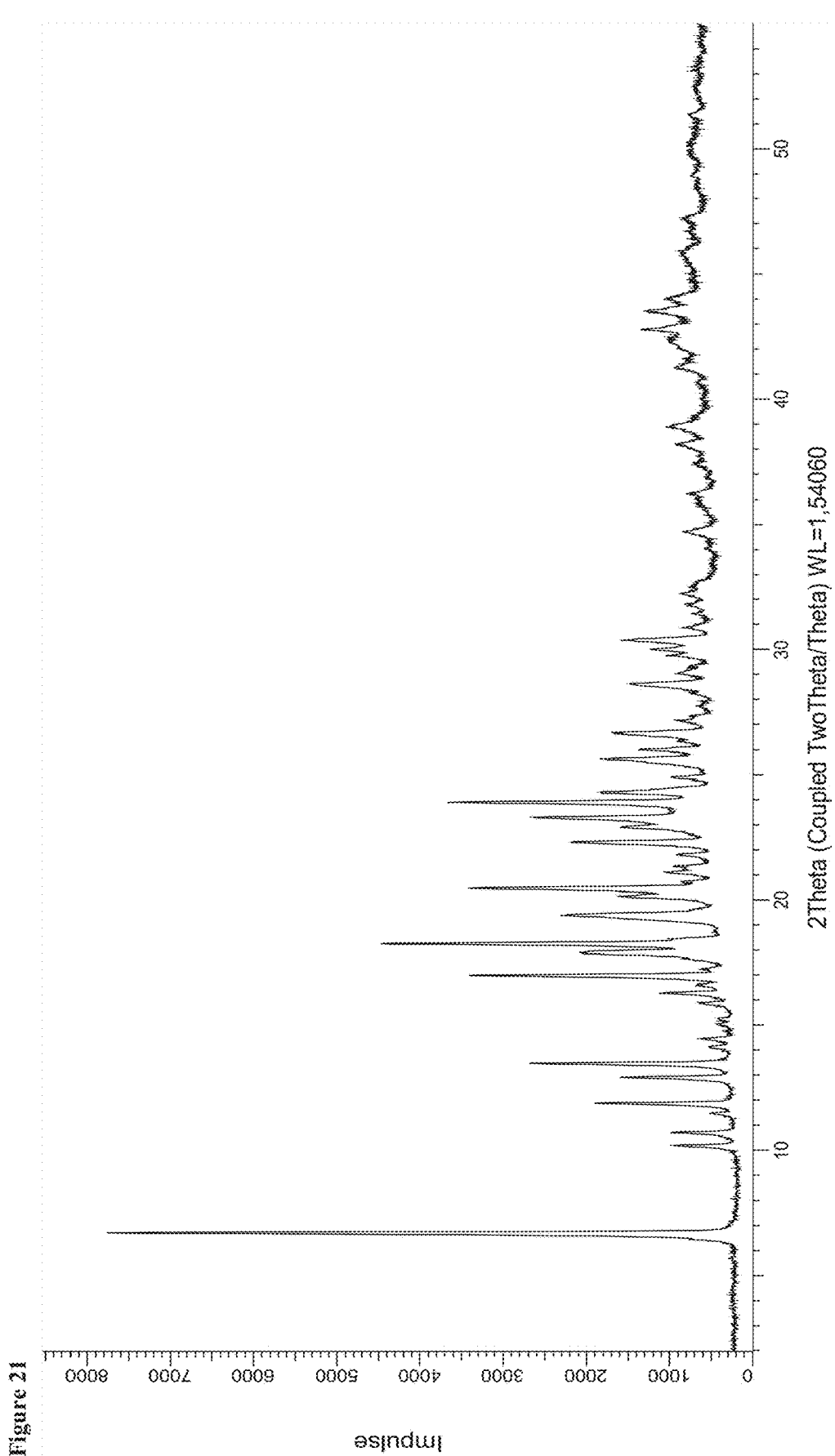
FIG. 21 shows a XRPD diffractogram of the besylate addition salt of (8-chloro-quinolin-2-yl)-(4-trifluoromethoxyphenyl)-amine.

A characteristic x-ray powder diffractogram is given in FIG. 21 and its characteristic signals are summarized in the following table:

| Index | Angle | Relative Intensity |
|---|---|---|
| 1 | 6.7 | 100.0% |
| 2 | 10.2 | 10.0% |
| 3 | 10.7 | 8.5% |
| 4 | 11.5 | 3.9% |
| 5 | 11.9 | 21.5% |
| 6 | 12.9 | 18.5% |
| 7 | 13.5 | 32.8% |
| 8 | 14.1 | 3.3% |
| 9 | 14.5 | 5.3% |
| 10 | 15.1 | 2.0% |
| 11 | 15.3 | 2.3% |
| 12 | 15.9 | 4.2% |
| 13 | 16.3 | 11.3% |
| 14 | 16.6 | 4.7% |
| 15 | 17.0 | 40.2% |
| 16 | 17.3 | 3.2% |
| 17 | 17.9 | 23.8% |
| 18 | 17.9 | 24.5% |
| 19 | 18.3 | 58.5% |
| 20 | 19.4 | 26.7% |
| 21 | 20.2 | 15.6% |
| 22 | 20.5 | 41.8% |
| 23 | 21.1 | 7.4% |
| 24 | 21.8 | 4.7% |
| 25 | 22.3 | 23.5% |
| 26 | 22.9 | 14.7% |
| 27 | 23.3 | 29.9% |
| 28 | 23.9 | 43.2% |
| 29 | 24.3 | 18.6% |
| 30 | 24.9 | 5.6% |
| 31 | 25.6 | 17.1% |
| 32 | 26.0 | 11.6% |
| 33 | 26.7 | 14.7% |
| 34 | 27.2 | 4.8% |
| 35 | 28.6 | 12.9% |
| 36 | 29.1 | 4.8% |
| 37 | 29.8 | 7.5% |
| 38 | 30.0 | 10.0% |
| 39 | 30.4 | 14.3% |
| 40 | 30.9 | 5.1% |
| 41 | 32.2 | 4.8% |
| 42 | 34.8 | 4.5% |
| 43 | 38.2 | 5.7% |
| 44 | 38.9 | 6.3% |
| 45 | 42.8 | 9.5% |
| 46 | 43.5 | 9.1% |

8. Preparation of (8-chloro-quinolin-2-yl)-(4-trifluoromethoxyphenyl)-amine (Tosylate Addition Salt)

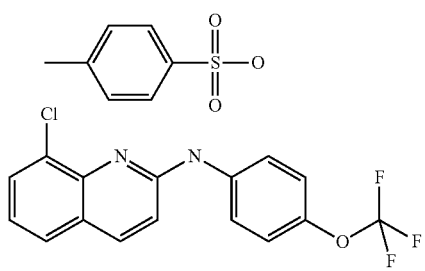

(8-Chloro-quinolin-2-yl)-(4-trifluoromethoxyphenyl)-amine (5 g; 14.8 mmol) was dissolved in diethyl ether (200 mL) at room temperature and toluenesulfonic acid (3.44 g; 17.7 mmol) dissolved in dichloromethane (10 mL) and methanol (2 mL) was added subsequently. The resulting slurry was stirred for 30 min before the precipitate was filtered off and dried under reduced pressure. The TolSO$_3$H addition salt was obtained as a pale yellow solid.

Yield: 7.5 g (99.4%).

Chemical purity: 99.9% (peak area at $\lambda$=254 nm).

Figure 12:
FIG. 12 shows a 1H-NMR spectrum of the tosylate addition salt of (8-chloro-quinolin-2-yl)-(4-trifluoromethoxyphenyl)-amine.
Figure 13:
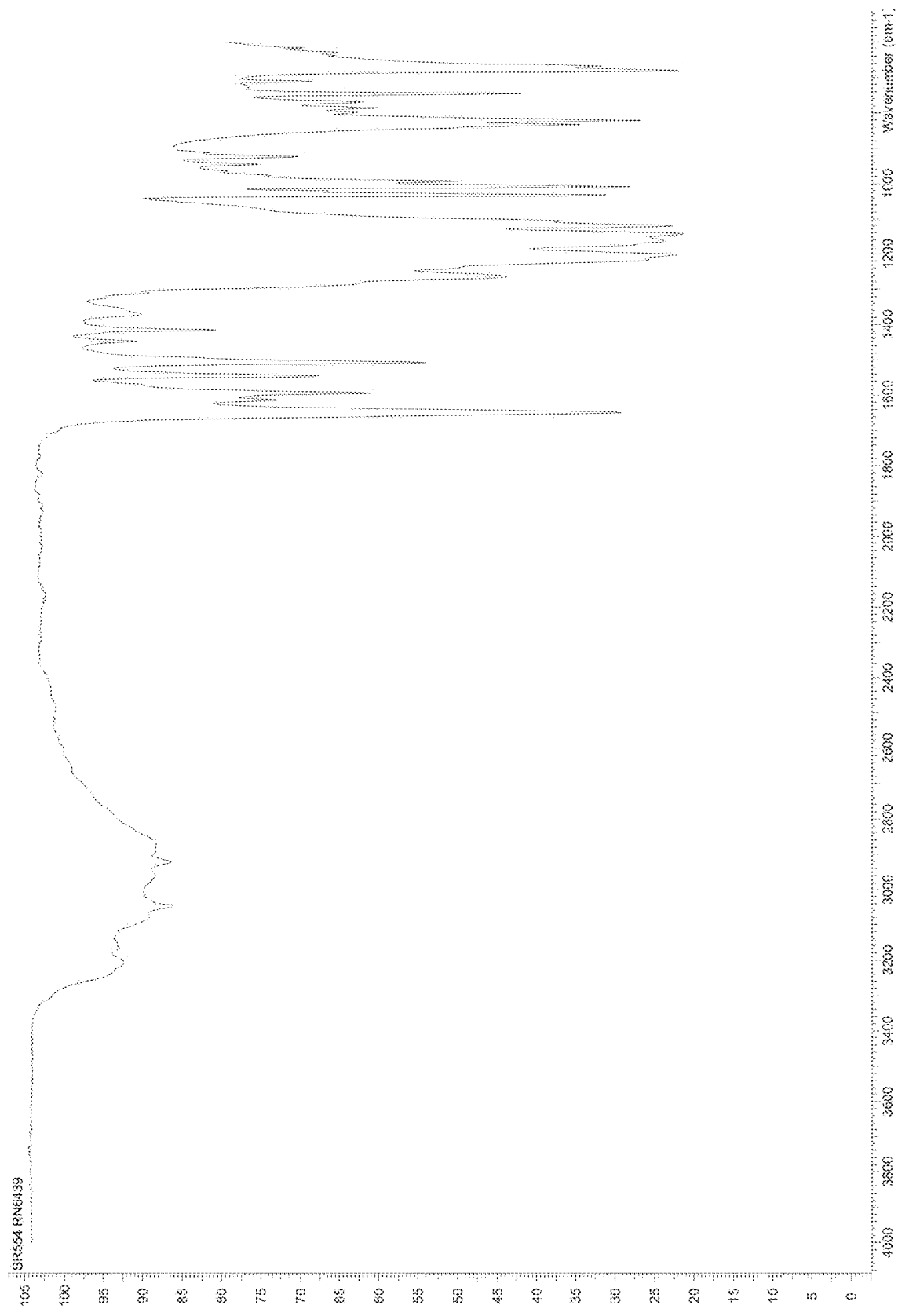
FIG. 13 shows a FT-IR spectrum of the tosylate addition salt of (8-chloro-quinolin-2-yl)-(4-trifluoromethoxyphenyl)-amine.

The identity of ABX-464-tosylate was verified by 1H-NMR (FIG. 12) and FT-IR (FIG. 13).

The NMR spectrum was characterized by the following signals:

1H NMR (400 MHz, DMSO-d6) δ ppm 2.29 (s, 3H); 7.12-7.18 (m, 3H); 7.24-7.42 (m, 3H); 7.50 (d, J=8.07 Hz, 2H); 7.75-7.81 (m, 2H); 8.17 (d, J=8.93 Hz, 1H); 8.30 (m, 2H); 9.96 (s, 1H); 11.00 (br s, 1H).

The IR-spectrum was characterized by the following signals:

1649; 1593; 1508; 1416; 1203; 1144; 1120; 1105; 1032; 1020; 1009; 993; 924; 833; 822; 746; 712; 681; 667 cm$^{-1}$.

Figure 22:
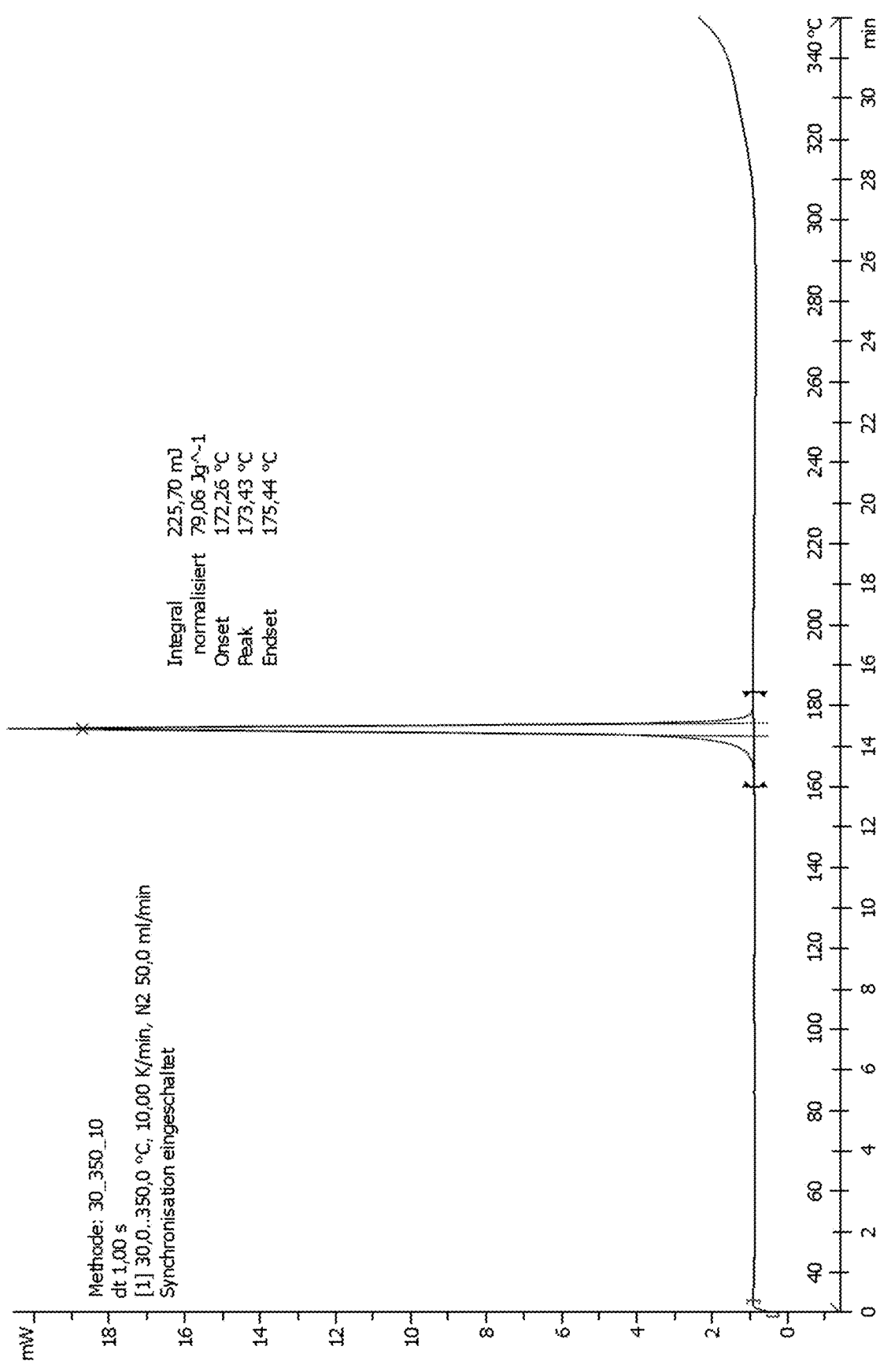
FIG. 22 shows a DSC thermogram of the tosylate addition salt of (8-chloro-quinolin-2-yl)-(4-trifluoromethoxyphenyl)-amine.

The solid state characteristics were investigated by means of DSC and XRPD and is as follows:

The DSC thermogram (FIG. 22) is characterized by a single endotherm with an onset temperature of 172° C. (±5° C.) and a peak temperature of 173° (±5° C.).

Figure 23:
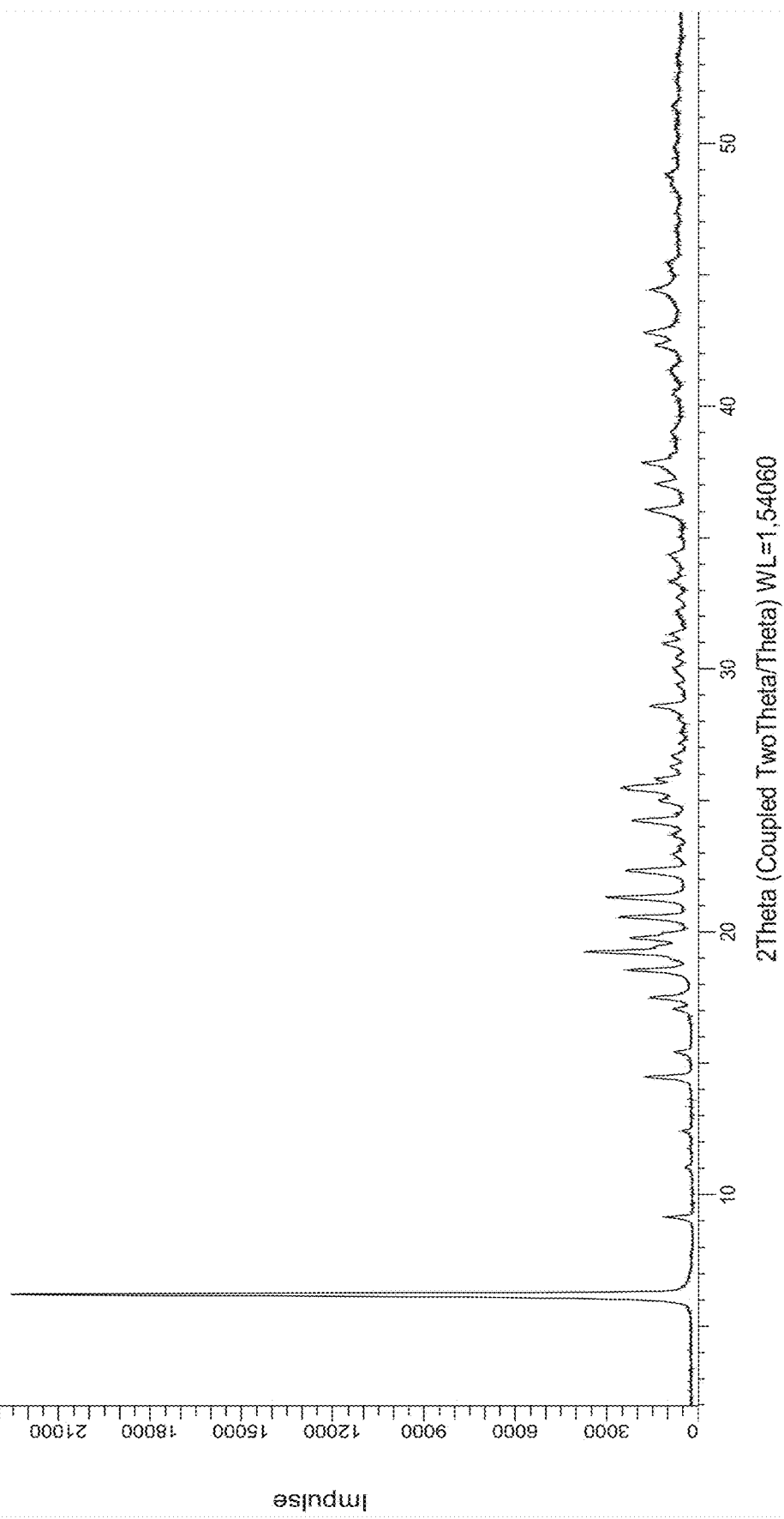
FIG. 23 shows a XRPD diffractogram of the tosylate addition salt of (8-chloro-quinolin-2-yl)-(4-trifluoromethoxyphenyl)-amine.

A characteristic x-ray powder diffractogram is given in FIG. 23 and its characteristic signals are summarized in the following table:

| Index | Angle | Relative Intensity |
|---|---|---|
| 1 | 6.2 | 100.0% |
| 2 | 9.1 | 3.6% |
| 3 | 11.1 | 1.2% |
| 4 | 12.5 | 1.5% |
| 5 | 14.5 | 7.1% |
| 6 | 15.4 | 2.4% |
| 7 | 17.1 | 2.6% |
| 8 | 17.5 | 6.0% |
| 9 | 18.5 | 9.4% |
| 10 | 19.2 | 15.7% |
| 11 | 19.8 | 8.6% |
| 12 | 20.6 | 10.1% |
| 13 | 21.3 | 12.1% |
| 14 | 22.3 | 8.7% |
| 15 | 23.0 | 1.7% |
| 16 | 23.7 | 1.6% |
| 17 | 24.2 | 8.0% |
| 18 | 25.0 | 3.5% |
| 19 | 25.5 | 9.6% |
| 20 | 25.8 | 4.3% |
| 21 | 26.3 | 2.0% |
| 22 | 26.7 | 1.9% |
| 23 | 28.6 | 5.2% |
| 24 | 31.0 | 3.2% |
| 25 | 31.4 | 2.2% |
| 26 | 33.3 | 1.8% |
| 27 | 34.4 | 2.2% |
| 28 | 36.0 | 5.0% |
| 29 | 37.0 | 3.7% |
| 30 | 37.8 | 5.8% |
| 31 | 42.3 | 3.6% |
| 32 | 42.8 | 5.2% |
| 33 | 44.4 | 4.2% |

9. Preparation of (8-chloro-quinolin-2-yl)-(4-trifluoromethoxyphenyl)-amine (Hemiedisylate Addition Salt)

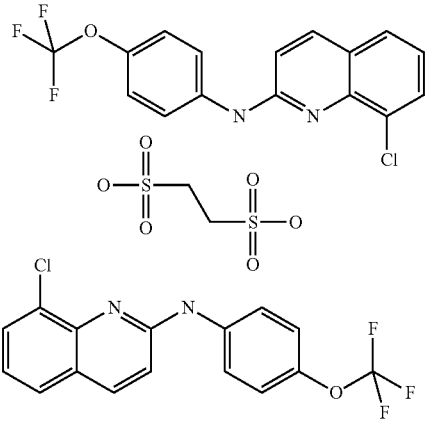

(8-Chloro-quinolin-2-yl)-(4-trifluoromethoxyphenyl)-amine (2 g; 5.9 mmol) was dissolved in diethyl ether (80 mL) at room temperature and ethanedisulfonic acid (0.74 g; 3.1 mmol) dissolved in acetone (6 mL) was added subsequently. The resulting slurry was stirred for 30 min before the precipitate was filtered off and dried under reduced pressure. The $Et(SO_3H)_2$ addition salt was obtained as a pale yellow solid.

Yield: 2.11 g (82%).

Chemical purity: 99.9% (peak area at λ=254 nm).

Figure 14:
FIG. 14 shows a 1H-NMR spectrum of the edisylate addition salt of (8-chloro-quinolin-2-yl)-(4-trifluoromethoxyphenyl)-amine.
Figure 15:
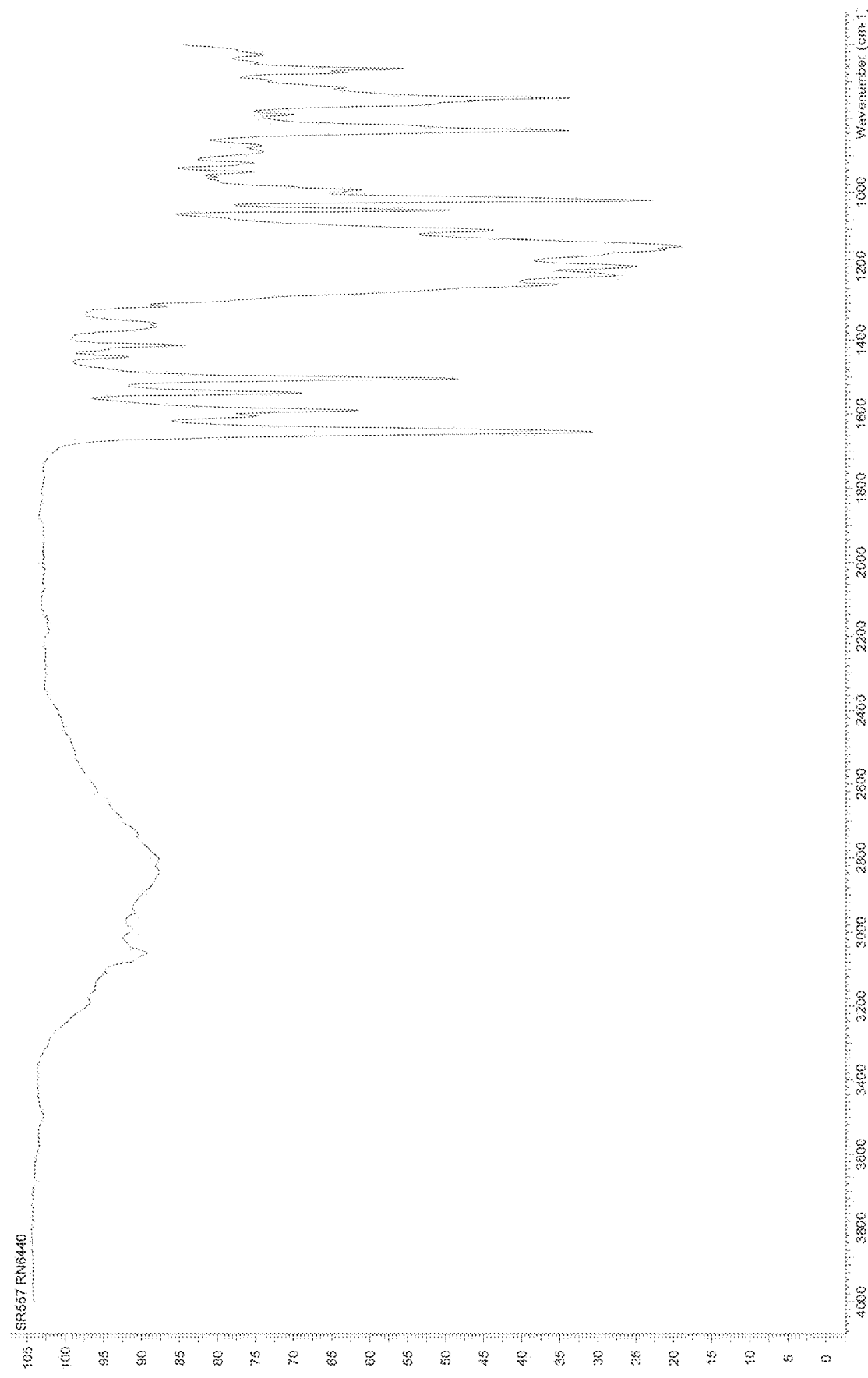
FIG. 15 shows a FT-IR spectrum of the edisylate addition salt of (8-chloro-quinolin-2-yl)-(4-trifluoromethoxyphenyl)-amine.

The identity of the hemiedisylate addition salt was verified by 1H-NMR (FIG. 14) and FT-IR (FIG. 15).

The NMR spectrum was characterized by the following signals:

1H NMR (400 MHz, DMSO-d6) δ ppm 2.76 (s, 2H); 7.17 (d, J=8.93 Hz, 1H); 7.23-7.42 (m, 3H); 7.75-7.81 (m, 2H); 8.17 (d, J=8.93 Hz, 1H); 8.30 (m, 2H); 9.97 (s, 1H); 10.87 (br s, 1H).

The IR-spectrum was characterized by the following signals:

1649; 1589; 1504; 1224; 1146; 1049; 1022; 833; 744; 665 cm-1.

Figure 24:
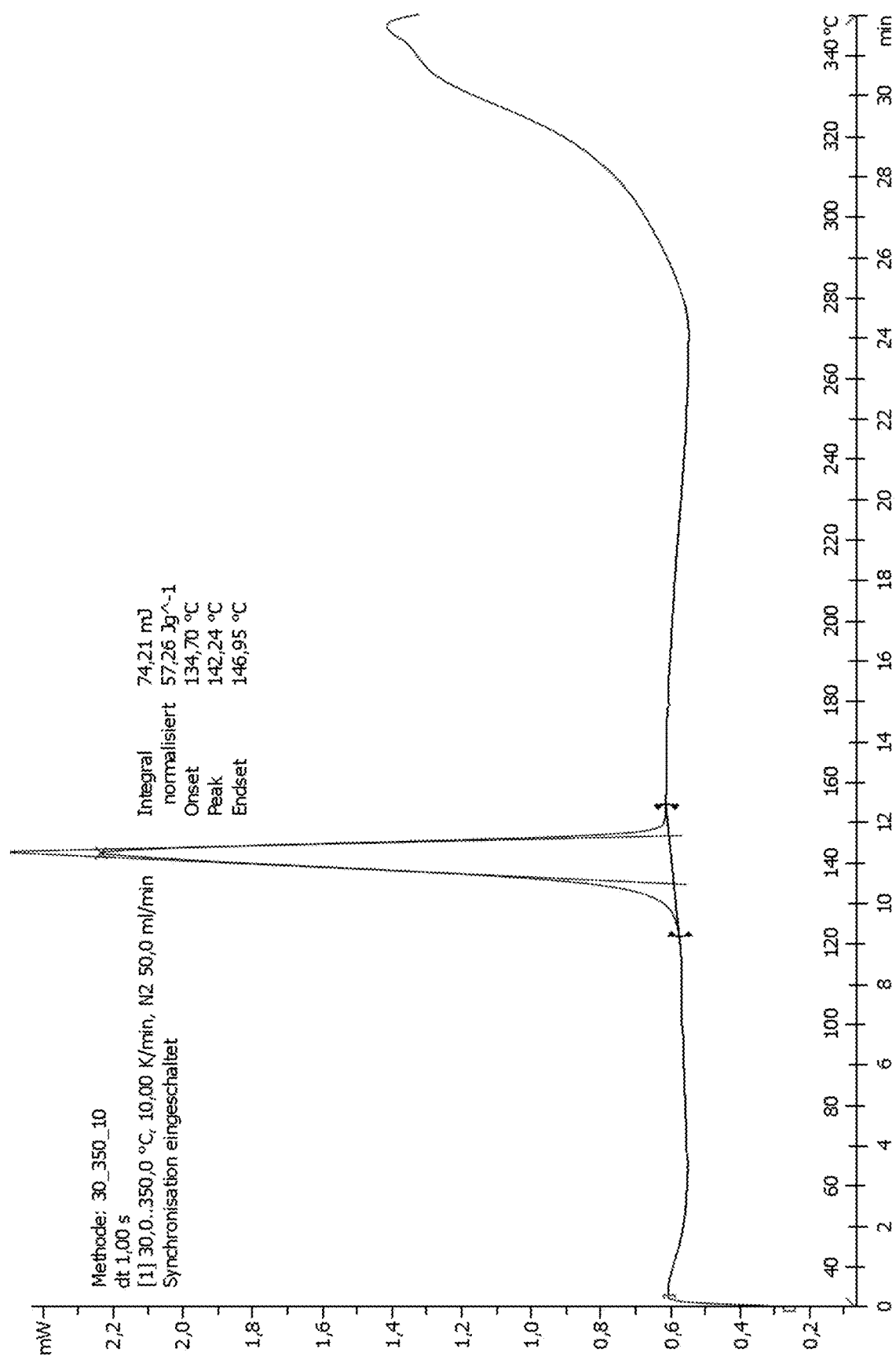
FIG. 24 shows a DSC thermogram of the hemiedisylate addition salt of (8-chloro-quinolin-2-yl)-(4-trifluoromethoxyphenyl)-amine.

The solid state characteristics were investigated by means of DSC and XRPD and is as follows:

The DSC thermogram (FIG. 24) is characterized by a broad single endotherm with an onset temperature of 142° C. (±5° C.) and a peak temperature of 173° (±5° C.).

Figure 25:
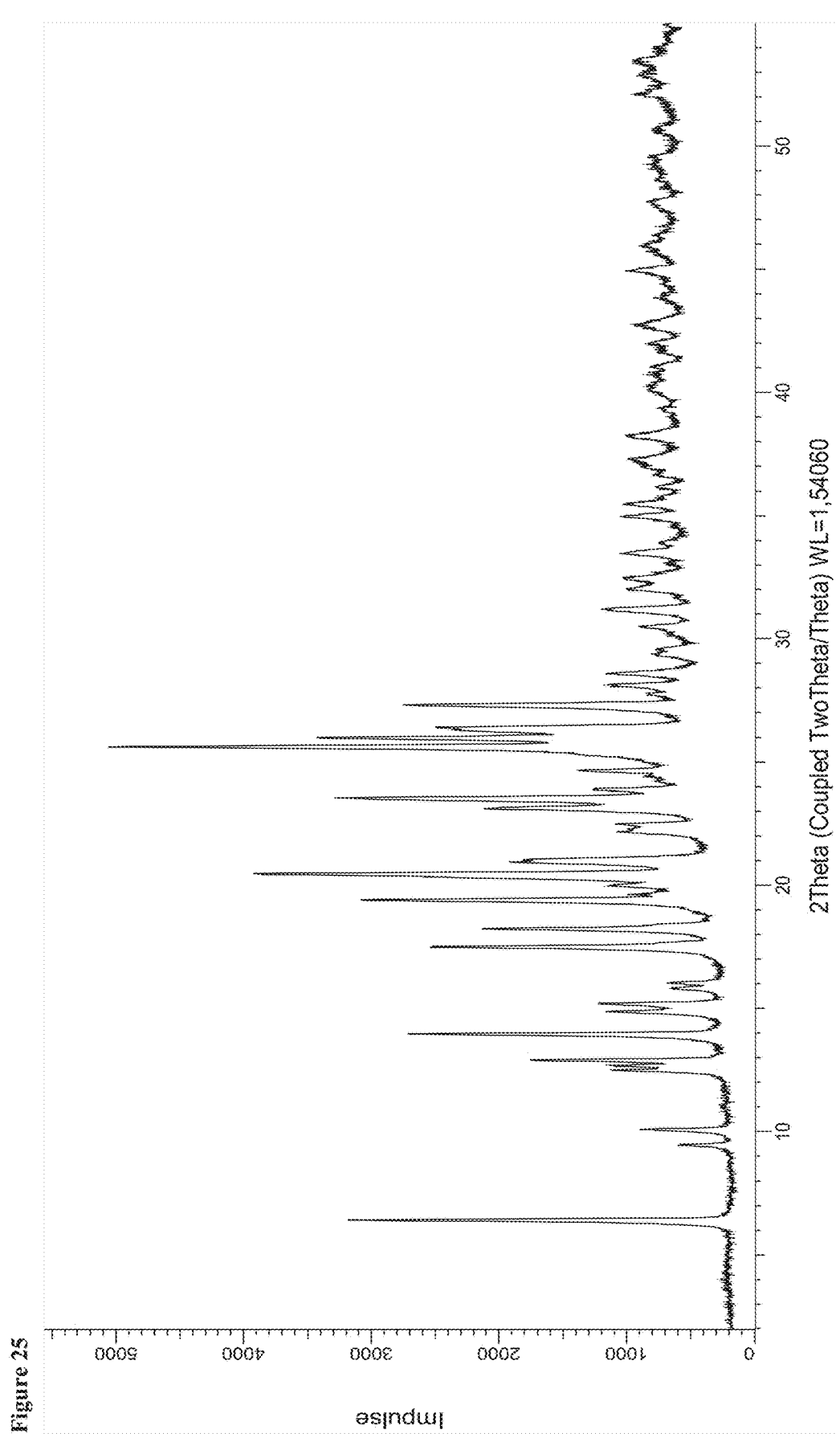
FIG. 25 shows a XRPD diffractogram of the hemiedisylate addition salt of (8-chloro-quinolin-2-yl)-(4-trifluoromethoxyphenyl)-amine.
Figure 26:
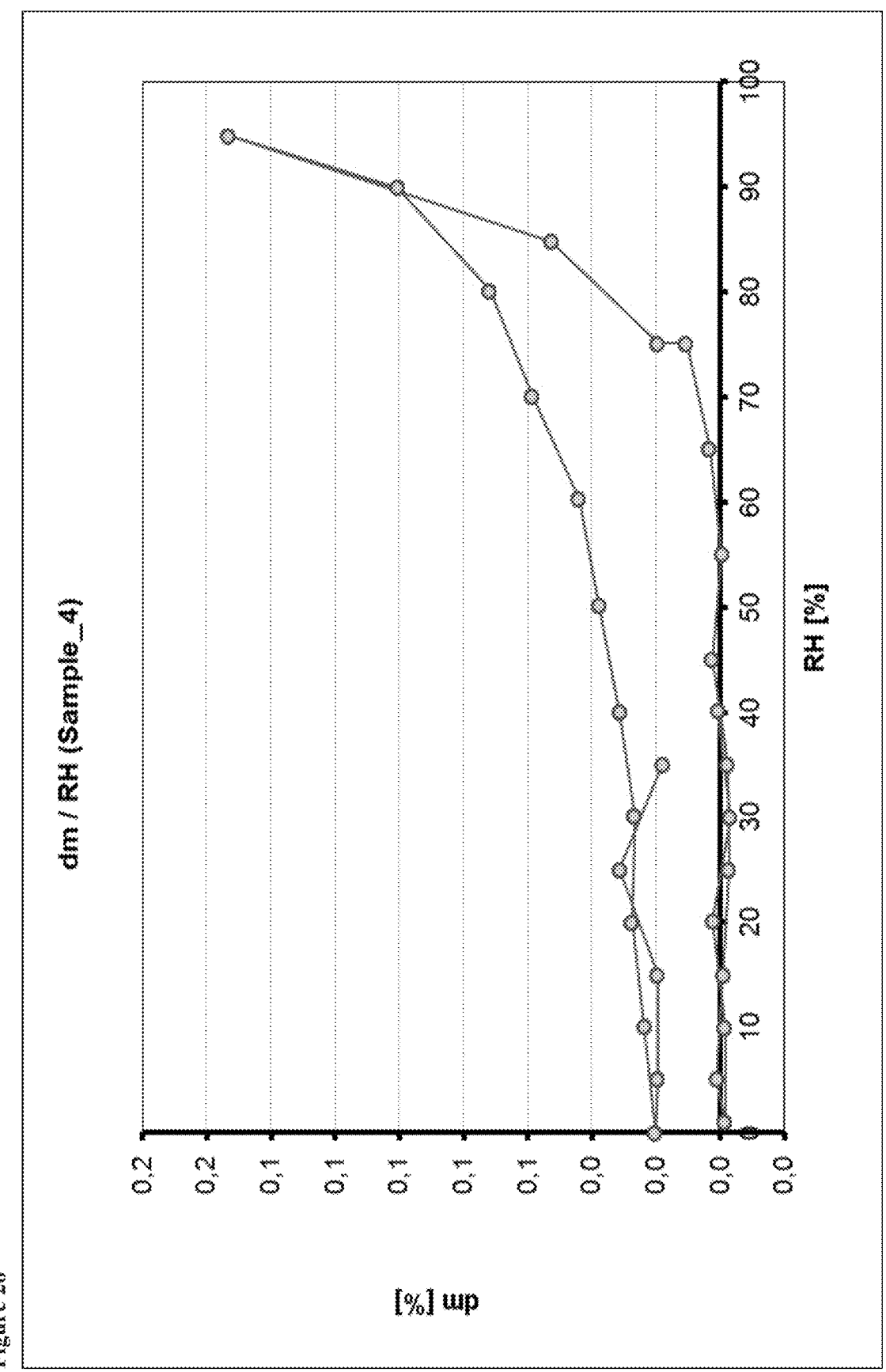
FIG. 26 shows the DVS diagram of the free base of (8-chloro-quinolin-2-yl)-(4-trifluoromethoxyphenyl)-amine.
Figure 27:
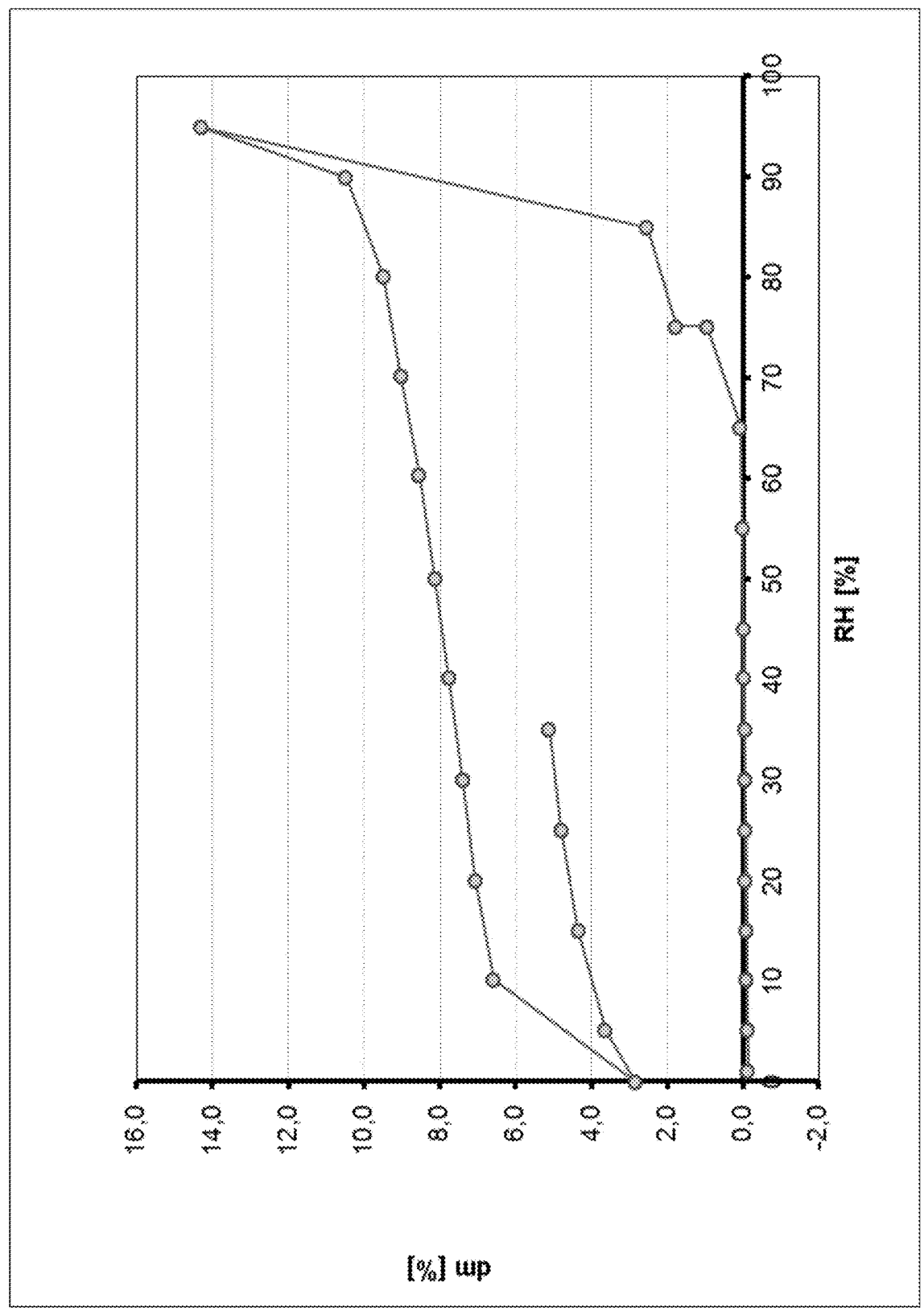
FIG. 27 shows the DVS diagram of the HCl addition salt of (8-chloro-quinolin-2-yl)-(4-trifluoromethoxyphenyl)-amine.
Figure 28:
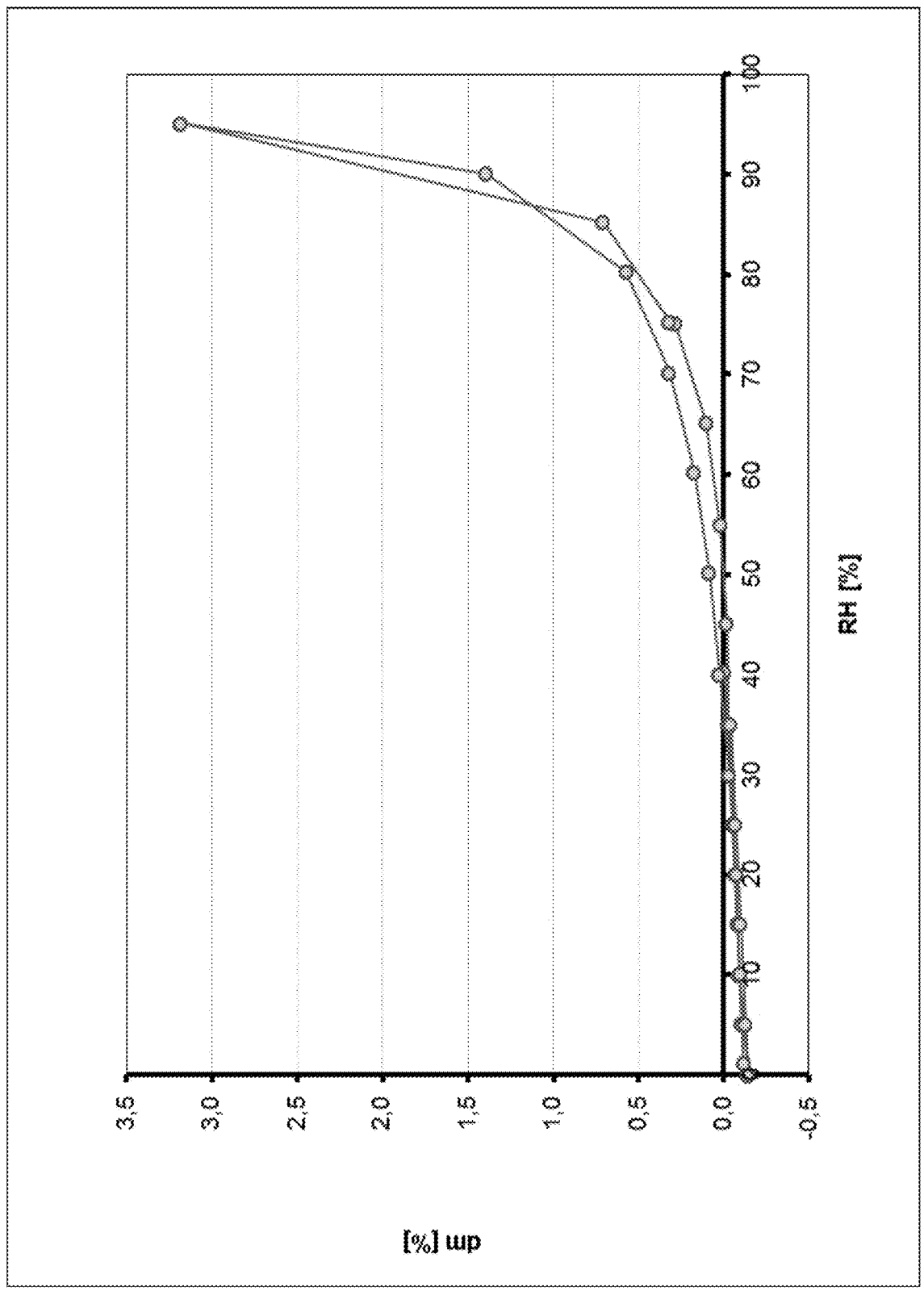
FIG. 28 shows the DVS diagram of the H₂SO₄ addition salt of (8-chloro-quinolin-2-yl)-(4-trifluoromethoxyphenyl)-amine.
Figure 29:
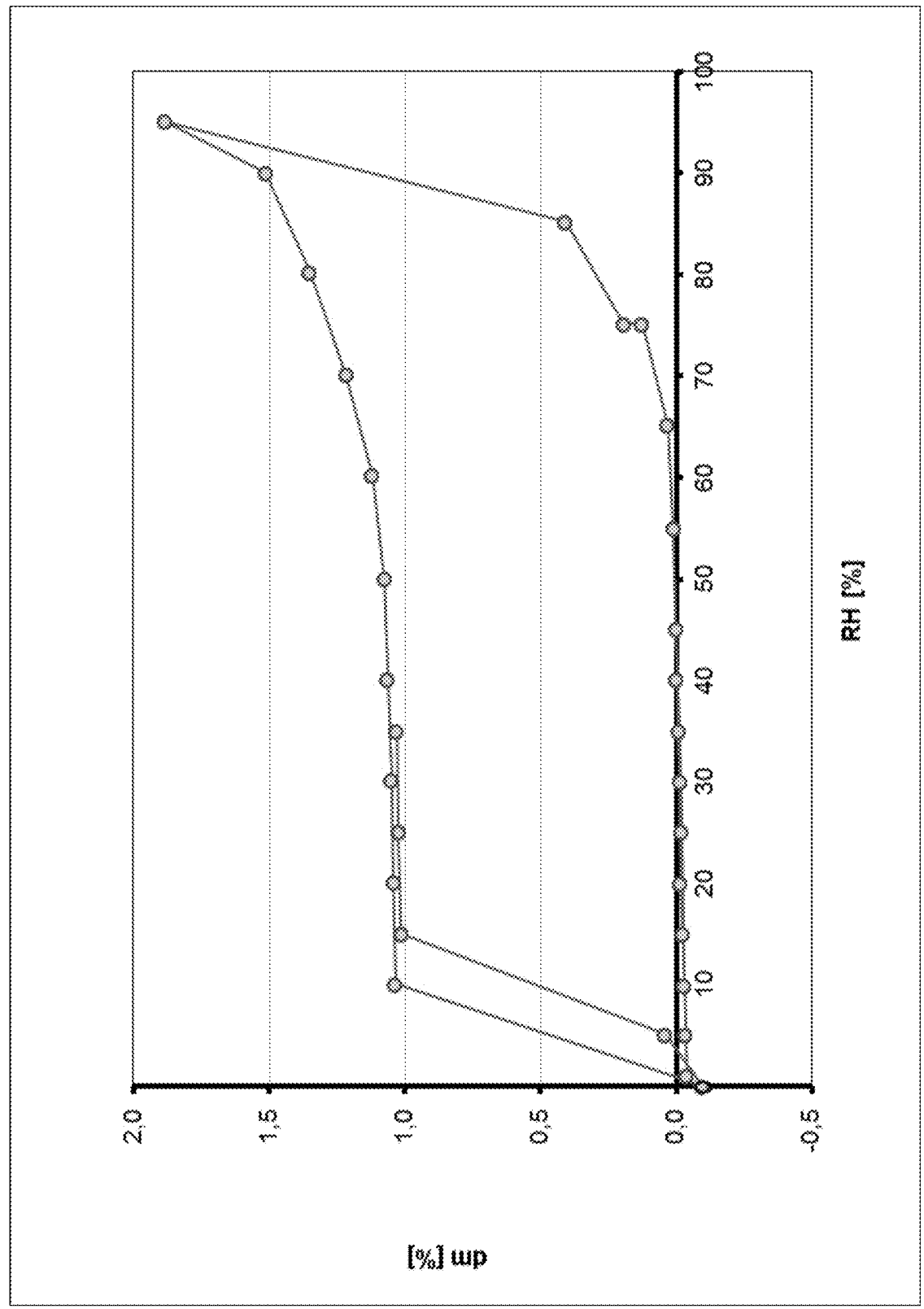
FIG. 29 shows the DVS diagram of the besylate addition salt of (8-chloro-quinolin-2-yl)-(4-trifluoromethoxyphenyl)-amine.
Figure 30:
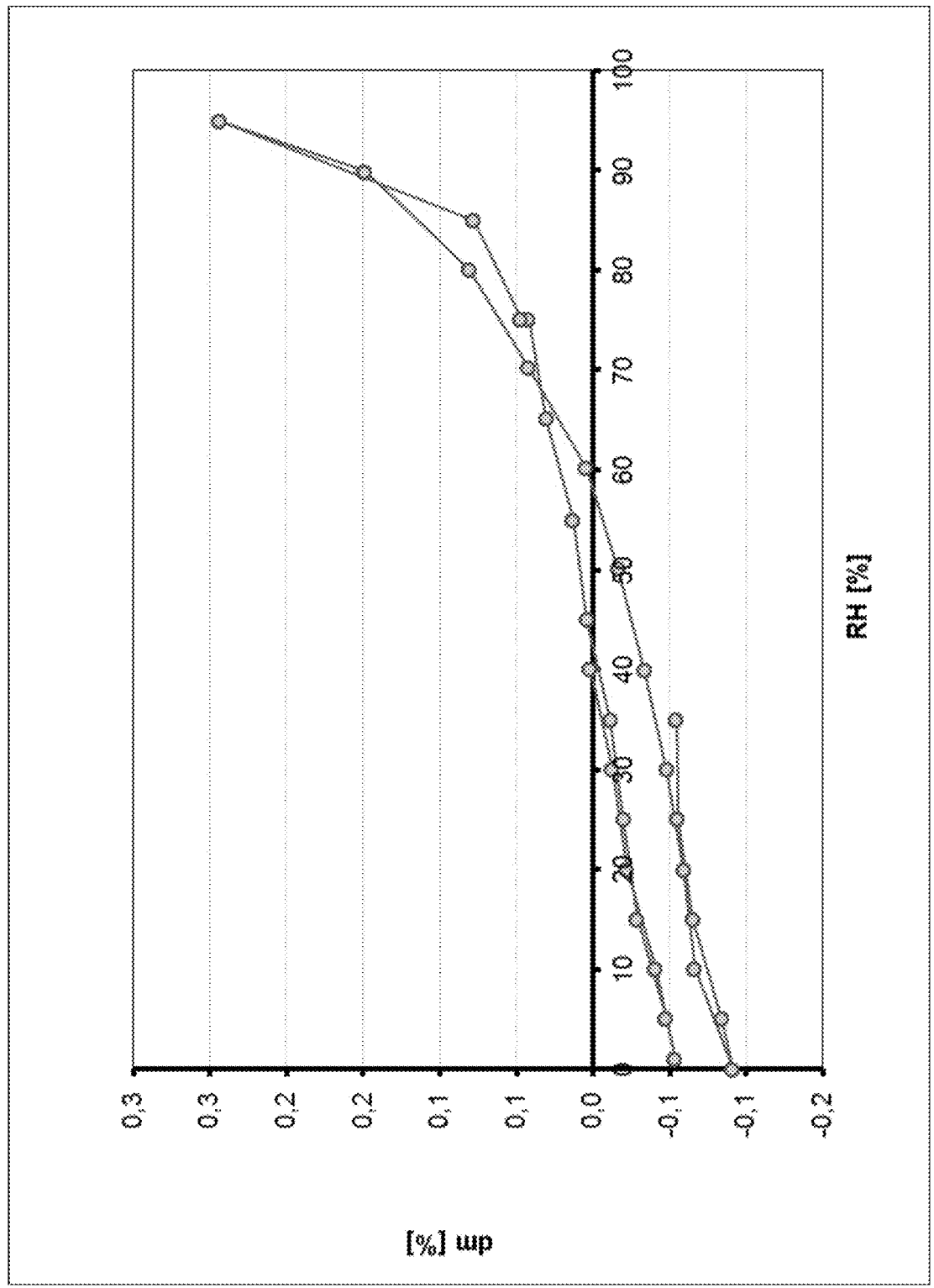
FIG. 30 shows the DVS diagram of the tosylate addition salt of (8-chloro-quinolin-2-yl)-(4-trifluoromethoxyphenyl)-amine.
Figure 31:
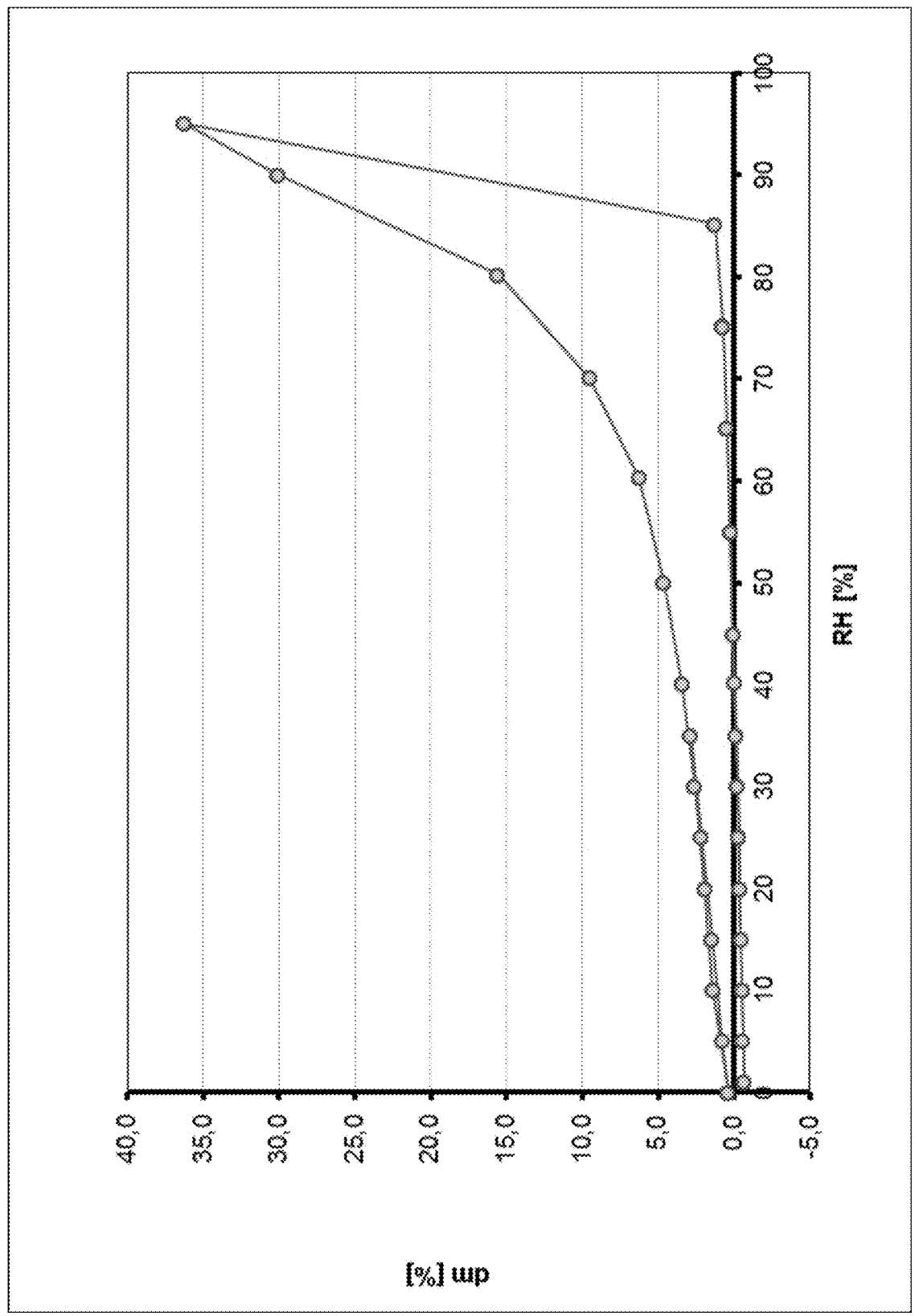
FIG. 31 shows the DVS diagram of the hemiedisylate addition salt of (8-chloro-quinolin-2-yl)-(4-trifluoromethoxyphenyl)-amine.

A characteristic x-ray powder diffractogram is given in FIG. 25 and its characteristic signals are summarized in the following table:

| Index | Angle | Relative Intensity |
|---|---|---|
| 1 | 6.4 | 60.2% |
| 2 | 9.4 | 8.9% |
| 3 | 10.1 | 13.2% |
| 4 | 12.5 | 15.6% |
| 5 | 12.7 | 19.0% |
| 6 | 12.9 | 32.1% |
| 7 | 14.0 | 50.2% |
| 8 | 14.9 | 19.5% |
| 9 | 15.2 | 19.5% |
| 10 | 15.8 | 8.0% |
| 11 | 16.0 | 8.5% |
| 12 | 17.5 | 49.3% |
| 13 | 18.2 | 39.5% |
| 14 | 19.4 | 58.5% |
| 15 | 20.0 | 16.1% |
| 16 | 20.4 | 76.4% |
| 17 | 21.0 | 30.4% |
| 18 | 22.2 | 11.7% |
| 19 | 22.4 | 11.7% |
| 20 | 23.1 | 35.6% |
| 21 | 23.5 | 57.0% |
| 22 | 23.9 | 16.6% |
| 23 | 24.7 | 17.7% |
| 24 | 25.6 | 100.0% |
| 25 | 26.0 | 63.3% |
| 26 | 26.4 | 39.6% |
| 27 | 27.3 | 47.4% |
| 28 | 28.1 | 12.4% |
| 29 | 28.6 | 14.3% |
| 30 | 31.2 | 13.7% |
| 31 | 32.0 | 9.9% |
| 32 | 32.4 | 10.3% |
| 33 | 33.5 | 9.7% |
| 34 | 35.0 | 9.3% |
| 35 | 35.5 | 9.5% |

10. Aqueous Solubility

The solubility properties of the generated solid states were studied in four different aqueous buffers with distinct pH values. Approximately 250 mg of each sample was mixed with 2.5 ml solvent and stirred. The solubility was determined at 15 min and 1 h.

It turned out that most of the acid addition salts showed very good solubility in aqueous solutions. A second result is, that the acid addition salts with inorganic counterion (HCl, $H_2SO_4$) exhibit first-rate solubility. The following table presents a summary of the results of all analyzed samples:

| | | Solubility [mg/mL] | | | | | |
|---|---|---|---|---|---|---|---|
| | | free base | HCl | $H_2SO_4$ | besylate | tosylate | hemi-edisylate |
| 0.01N HCl pH ~2.2 | 15 min | 0.003 | 0.116 | 0.089 | 0.023 | 0.006 | 0.075 |
| | 1 h | 0.004 | 0.147 | 0.152 | 0.032 | 0.010 | 0.065 |
| 20 mM Na-acetate pH 4.5 | 15 min | 0 | 0.074 | 0.093 | 0.024 | 0 | 0.048 |
| | 1 h | 0 | 0.136 | 0.139 | 0.016 | 0.003 | 0.050 |

-continued

| | | Solubility [mg/mL] | | | | | |
|---|---|---|---|---|---|---|---|
| | | free base | HCl | $H_2SO_4$ | besylate | tosylate | hemi-edisylate |
| 50 mM $KH_2PO_4$ pH 6.8 | 15 min | 0 | 0.068 | 0.035 | 0.003 | 0 | 0.018 |
| | 1 h | 0 | 0.104 | 0.114 | 0.007 | 0 | 0.023 |
| FaSSiF (SIF-powder) | 15 min | 0.064 | 0.111 | 0.109 | 0.077 | 0.030 | — |
| | 1 h | 0.061 | 0.198 | 0.157 | 0.045 | 0.013 | — |

11. Hygroscopicity

The hygroscopicity was determined by Dynamic Vapor Sorption Analysis (DVS). Approximately 200 mg of each solid state were weight on a sample plate and subjected to the apparatus. The humidity inside was varied in a range from 0 to 95% RH and the mass change (dm [%]) of the samples measured continuously.

It turned out that the free base absorbs more or less not any humidity. The same applies for the tosylate salt, whereas besylate and sulfate exhibit at least a low hygroscopicity with up to 1.9 and 3.2% weight increase, respectively. But it was demonstrated that this water uptake is reversible at least and not or only minor (besylate) associated with changes of the crystalline form. An opposing behavior was observed for the hemiedisyalte and hydrochloride salt, where a weight increase was detected that even was irreversible. Moreover, this water absorption is closely connected with significant changes of the initial crystalline form. The following table presents a summary of the relative weight change observed during the DVS experiment (FIG. 26-31):

| | Relative weight change (dm) [%] | | | | | | |
|---|---|---|---|---|---|---|---|
| RH [%] | 40 | →0 | →75 | →95 | →40 | →0 | →35 |
| Free base (FIG. 25) | 0 | 0 | 0.02 | 0.15 | 0.03 | 0.02 | 0.02 |
| HCl salt (FIG. 26) | 0 | −0.11 | 1.7 | 14.3 | 7.8 | 2.8 | 5.1 |
| $H_2SO_4$ salt (FIG. 27) | 0 | −0.11 | 0.32 | 3.2 | 0.03 | −0.14 | −0.04 |
| Besylate salt (FIG. 28) | 0 | −0.04 | 0.19 | 1.9 | 1.1 | −0.09 | 1.0 |
| Tosylate salt (FIG. 29) | 0 | −0.05 | 0.05 | 0.24 | −0.03 | −0.09 | −0.05 |
| Hemiedisylate salt (FIG. 30) | 0 | −0.65 | 0.74 | 36.2 | 3.5 | 0.4 | 2.9 |

What is claimed is:

1. A crystalline form of a sulfate salt of (8-chloro-quinolin-2-yl)-(4-trifluoromethoxyphenyl)-amine, characterized by data which is one or more of the following:
   (a) An XRPD pattern having peaks at 6.7, 11.6, 17.3, 20.3, and 26.4 degrees 2-theta±0.2 degrees 2-theta;
   (b) An XRPD pattern substantially as depicted in FIG. 19;
   (c) An IR spectrum having peaks at 1660, 1508, 1269, 1144, 1018, 993, 864, 746, and 669 $cm^{-1}$.

2. The crystalline form of the sulfate salt of (8-chloro-quinolin-2-yl)-(4-trifluoromethoxyphenyl)-amine of claim 1, wherein the XRPD pattern further includes one, two, three, four or five additional peaks at 13.8, 15.6, 22.1, 24.0 and 28.3 degrees 2-theta±0.2 degrees 2-theta.

3. A crystalline form of a besylate salt of (8-chloro-quinolin-2-yl)-(4-trifluoromethoxyphenyl)-amine, characterized by data which is one or more of the following:
   (a) An XRPD pattern having peaks at 6.7, 17.0, 18.3, 20.5, and 23.9 degrees 2-theta±0.2 degrees 2-theta;
   (b) An XRPD pattern substantially as depicted in FIG. 21;
   (c) An IR spectrum having peaks at 1647, 1506, 1151, 1028, 1010, 995, 923, 831, 758, 748, 725, 696, 669, and 607 $cm^{-1}$.

4. The crystalline form of the besylate salt of (8-chloro-quinolin-2-yl)-(4-trifluoromethoxyphenyl)-amine of claim 3, wherein the XRPD pattern further includes one, two or three additional peaks at 11.5, 13.5 and 19.4 degrees 2-theta±0.2 degrees 2-theta.

5. A crystalline form of a tosylate salt of (8-chloro-quinolin-2-yl)-(4-trifluoromethoxyphenyl)-amine, characterized by data which is one or more of the following:
   (a) An XRPD pattern having peaks at 6.2, 19.2, 20.6, 21.3, and 25.5 degrees 2-theta±0.2 degrees 2-theta;
   (b) An XRPD pattern substantially as depicted in FIG. 23;
   (c) An IR spectrum having peaks at 1649, 1593, 1508, 1416, 1203, 1144, 1120, 1105, 1032, 1020, 1009, 993, 924, 833, 822, 746, 712, 681, and 667 $cm^{-1}$.

6. The crystalline form of the tosylate salt of (8-chloro-quinolin-2-yl)-(4-trifluoromethoxyphenyl)-amine of claim 5, wherein the XRPD pattern further includes one or two additional peaks at 9.1, 14.7 degrees 2-theta±0.2 degrees 2-theta.

7. A crystalline form of a Hydrochloride salt of (8-chloro-quinolin-2-yl)-(4-trifluoromethoxyphenyl)-amine, characterized by data which is one or more of the following:
   (a) An XRPD pattern having peaks at 5.8, 16.2, 18.6, 25.5, 27.7 degrees 2-theta±0.2 degrees 2-theta;
   (b) An XRPD pattern substantially as depicted in FIG. 17;
   (c) An IR spectrum having peaks at 1645, 1577, 1547, 1504, 1409, 1263, 1199, 1172, 1107, 1014, 999, 987, 922, 840, 783, 767, 742, 667, 628 $cm^{-1}$.

8. The crystalline form of the Hydrochloride salt of (8-chloro-quinolin-2-yl)-(4-trifluoromethoxyphenyl)-amine of claim 7, wherein the XRPD pattern further includes one, two or three additional peaks at 12.9, 14.9, 25.9 degrees 2-theta±0.2 degrees 2-theta.

9. A pharmaceutical composition containing the crystalline form of the Hydrochloride salt of claim 7 and a pharmaceutically acceptable carrier.

10. The pharmaceutical composition of claim 9 for use in a method for treating an HIV infection.

* * * * *